United States Patent [19]

Johnson et al.

[11] Patent Number: 4,593,131
[45] Date of Patent: Jun. 3, 1986

[54] PHARMACOLOGICALLY ACTIVE 4-[2-HYDROXY-4-(SUBSTITUTED)PHENYL]-NAPHTHALEN-2(1H)-ONES AND 2-OLS, DERIVATIVES THEREOF AND INTERMEDIATES THEREFOR

[75] Inventors: Michael R. Johnson, Gales Ferry; Lawrence S. Melvin, Jr., Ledyard, both of Conn.

[73] Assignee: Pfizer Inc., New York, N.Y.

[21] Appl. No.: 651,541

[22] Filed: Sep. 17, 1984

Related U.S. Application Data

[62] Division of Ser. No. 326,952, Dec. 2, 1981, Pat. No. 4,486,609, which is a division of Ser. No. 244,435, Mar. 16, 1981, Pat. No. 4,331,602, which is a division of Ser. No. 189,402, Sep. 19, 1980, Pat. No. 4,285,867.

[51] Int. Cl.[4] .................. C07C 41/00; C07C 43/02
[52] U.S. Cl. .................. 568/632; 546/344; 568/734
[58] Field of Search .................. 568/734, 632; 546/347

[56] References Cited

U.S. PATENT DOCUMENTS

| | | | |
|---|---|---|---|
| 2,886,589 | 5/1959 | Novello .................. | 568/734 |
| 3,522,319 | 7/1970 | Bencze et al. .................. | 568/734 |
| 3,576,887 | 4/1971 | Hughes et al. .................. | 260/619 |
| 3,646,122 | 2/1972 | Bencze .................. | 568/734 |
| 3,862,986 | 1/1975 | Hellerbach .................. | 260/560.5 |
| 3,974,157 | 8/1976 | Shetty et al. .................. | 260/247.2 B |
| 4,285,867 | 8/1981 | Johnson et al. .................. | 546/344 |
| 4,306,097 | 12/1981 | Harbert et al. .................. | 568/731 |
| 4,366,328 | 12/1982 | Numata et al. .................. | 568/734 |
| 4,386,007 | 5/1983 | Kraus et al. .................. | 568/632 |
| 4,486,609 | 12/1984 | Johnson et al. .................. | 568/734 |

FOREIGN PATENT DOCUMENTS

| | | |
|---|---|---|
| 870402 | 3/1979 | Belgium . |
| 1062252 | 3/1967 | United Kingdom .................. 568/734 |

OTHER PUBLICATIONS

Chemical Abstracts, 85, 176952f (1976).

Primary Examiner—Ethel G. Love
Attorney, Agent, or Firm—Charles J. Knuth; Albert E. Frost; Peter C. Richardson

[57] ABSTRACT

Compounds having the formula

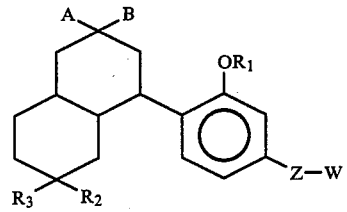

wherein

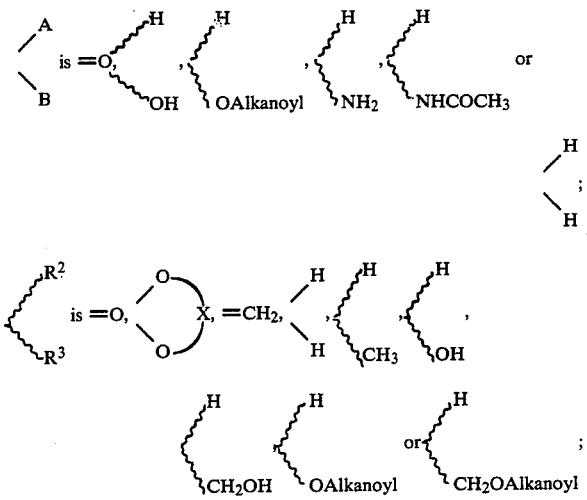

$R_1$ is hydrogen, benzyl or alkanoyl,
X is $C_{2-4}$ alkylene; and
Z-W is alkyl, phenylalkyl or pyridylalkyl which can have an oxygen atom as part of the alkyl chain and their use as CNS agents, antidiarrheals and antiemetics. Processes for their preparation and intermediates therefor are described.

12 Claims, No Drawings

PHARMACOLOGICALLY ACTIVE 4-[2-HYDROXY-4-(SUBSTITUTED)PHENYL]-NAPHTHALEN-2(1H)-ONES AND 2-OLS, DERIVATIVES THEREOF AND INTERMEDIATES THEREFOR

CROSS-REFERENCE TO RELATED APPLICATIONS

This application is a division of application Ser. No. 326,952, filed Dec. 2, 1981, now U.S. Pat. No. 4,486,609, issued Dec. 4, 1984 which in turn is a division of application Ser. No. 244,435, filed Mar. 16, 1981, now U.S. Pat. No. 4,331,602, issued May 25, 1982, which in turn is a division of application Ser. No. 189,402, filed Sept. 19, 1980, now U.S. Pat. No. 4,285,867, issued Aug. 25, 1981.

BACKGROUND OF THE INVENTION

This invention relates to novel 4-[2-hydroxy-4-(substituted)phenyl]-naphthalen-2(1H)-ones and 2-ols, to derivatives thereof, to processes for preparation of said compounds, and intermediates therefor. The naphthalen-2(1H)-one and 2-ol products are useful as CNS agents, especially as non-narcotic analgesics, antiemetics and antidiarrheals.

Despite the current availability of a number of analgesic agents, the search for new and improved agents useful for the control of broad levels of pain and accompanied by a minimum of side-effects continues. The most commonly used agent, aspirin, is of no practical value for the control of severe pain and is known to exhibit various undesirable side-effects. Other analgesic agents, such as meperidine, codeine, and morphine, possess addictive liability. The need for improved and potent analgesic agents is, therefore, evident.

Compounds having utility as analgesics, tranquilizers, sedatives, antianxiety agents and/or as anticonvulsants, diuretics and antidiarrheal agents are described in Belgian Pat. Nos. 870,404 and 870,402, both granted Mar. 12, 1979. Belgian Pat. No. 870,404 describes 3-[2-hydroxy-4-(substituted)phenyl]cycloalkanones and cycloalkanols; and Belgian Pat. No. 870,402 discloses certain 2-(acyclic substituted)phenols; namely, 2-(hydroxyalkyl)-4-(substituted)phenols and 2-(oxoalkyl)-4-(substituted)phenols.

U.S. Pat. No. 3,576,887, issued Apr. 27, 1971, discloses a series of 1-(1'-hydroxy)alkyl-2-(o-hydroxyphenyl)cyclohexanes which exhibit central nervous system depressant properties.

U.S. Pat. No. 3,974,157 describes 2-phenylcyclohexanones which can be substituted in the phenyl ring with up to two alkyl, hydroxy or alkoxy groups as intermediates for preparation of 1-(aminoalkyl)-2-phenylcyclohexanols useful as analgesics, local anesthetics and antiarrhythmics.

Chemical Abstracts 85, 176952f (1976) discloses a number of 3-phenyl- and 3-phenylalkylcyclohexanones as intermediates for 2-aminomethyl-3-phenyl (or phenylalkyl)cyclohexanones which exhibit analgesic, sedative, antidepressant and anticonvulsant activities.

Our concurrently filed application, D.P.C. (Ph) 6302, entitled "Pharmacologically Active 2-Hydroxy-4-(Substituted)Phenyl Cycloalkanes, Derivatives and Intermediates Therefor" describes 2-hydroxy-4-(substituted)cycloalkanones and cycloalkanols in which the 4- (or 5)-position of the cycloalkyl moiety is substituted with hydroxy or a substituted alkyl group.

SUMMARY OF THE INVENTION

The compounds of this invention have the formula

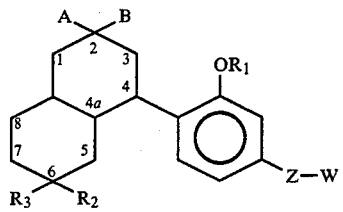

wherein
  A when taken individually is hydrogen;
  B when taken individually is hydroxy, or alkanoyloxy having from one to five carbon atoms,
  A and B when taken together are oxo;
  $R_1$ is hydrogen, benzyl, or $R_1'$ wherein $R_1'$ is alkanoyl having from one to five carbon atoms, $P(O)(OH)_2$ and mono- and disodium and potassium salts thereof, $-CO(CH_2)_2COOH$ and the sodium and potassium salts thereof, and $-CO(CH_2)_pNR_4R_5$ wherein p is 0 or an integer from 1 to 4, each of $R_4$ and $R_5$ when taken individually is hydrogen or alkyl having from one to four carbon atoms; $R_4$ and $R_5$ when taken together with the nitrogen to which they are attached form a 5- or 6-membered heterocyclic ring (piperidino, pyrrolo, pyrrolidino, morpholino and N-alkylpiperazino having from one to four carbon atoms in the alkyl group);
  $R_2$ when taken individually is hydrogen,
  $R_3$ when taken individually is hydrogen, methyl, hydroxy, hydroxymethyl, $OR_1'$ or $-CH_2OR_1'$;
  $R_2$ and $R_3$ when taken together are oxo, methylene or alkylenedioxy having from two to four carbon atoms;
  W is hydrogen, pyridyl or

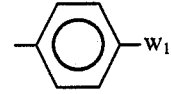

wherein $W_1$ is hydrogen, chloro or fluoro;
when W is hydrogen, Z is
  (a) alkylene having from five to thirteen carbon atoms; or
  (b) $-(alk_1)_m-O-(alk_2)_n-$ wherein each of $(alk_1)$ and $(alk_2)$ is alkylene having from one to thirteen carbon atoms; each of m and n is 0 or 1; with the provisos that the summation of carbon atoms in $(alk_1)$ plus $(alk_2)$ is not less than five or greater than thirteen; and at least one of m and n is 1;
when W is other than hydrogen, Z is
  (a) alkylene having from three to eight carbon atoms; or
  (b) $-(alk_1)_m-O-(alk_2)_n-$ wherein each of $(alk_1)$ and $(alk_2)$ is alkylene having from one to eight carbon atoms; each of m and n is 0 or 1; with the provisos that the summation of carbon atoms in $(alk_1)$ plus $(alk_2)$ is not less than three or greater than eight; and at least one of m and n is 1.

Also included in this invention as noted above are the pharmaceutically acceptable acid addition salts of those compounds of formula I which contain a basic group. Typical of such compounds are those wherein the W variable is pyridyl and/or $OR_1$ represents a basic ester moiety. In compounds having more than one basic group present, polyacid addition salts are, of course, possible. Representative of such pharmaceutically acceptable acid addition salts are the mineral acid salts such as the hydrochloride, hydrobromide, sulfate, phosphate, nitrate; organic acid salts such as the citrate, acetate, sulfosalicylate, tartrate, glycolate, malate, malonate, maleate, pamoate, salicylate, stearate, phthalate, succinate, gluconate, 2-hydroxy-3-naphthoate, lactate, mandelate and methanesulfonate.

Compounds having the above formula, and the pharmaceutically acceptable acid addition salts thereof, are effective as CNS agents, especially as analgesics in mammals, including humans; and/or as anti-emetics in mammals, including man.

Compounds of formula I wherein A is hydrogen and B is hydroxy contain asymmetic centers at the 2-, the 4-, the 4a-, and 8a- and the 6-positions and may of course, contain additional asymmetric centers in the —Z—W— substituent of the phenyl ring. Cis-relationship between the 2- and 4-position substituents of the bicyclic moiety is favored, as is trans-relationship between the 4a- and 8a-hydrogens, and between the 4-hydrogen and the 4a-hydrogen because of their quantitatively greater biological activity. For the same reason, trans-relationships at the 4-, 4a- and the 4a-, 8a-positions is favored for compounds wherein A and B when taken together represent oxo. The 6-substituted compounds of formula I exhibit potent biological activity regardless of whether the stereochemistry at said position is axial or equatorial.

In addition to the compounds of formula I, various intermediates useful in the preparation of said compounds are also included in this invention. The intermediates have formulae II–IV below:

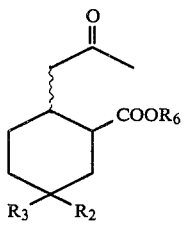
II

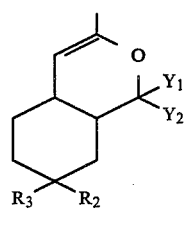
III

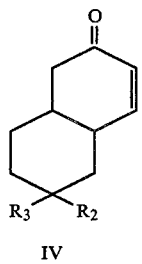
IV wherein $R_6$ is hydrogen or $C_{1-4}$ alkyl;

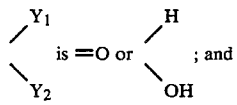
; and $R_2$ and $R_3$ are as previously defined. Also included in this invention are the ketoacids and the ketoaldehydes corresponding to formula III and which are obtained by cleavage of the enolic lactone or lactol, respectively.

It is noted that formula I compounds wherein $R_1$ is benzyl are not pharmacologically active for the purposes disclosed herein but are useful as intermediates to formula I compounds wherein $R_1$ is hydrogen.

For convenience, the above formula depicts the racemic compounds. However, formulae I–IV are considered to be generic to and embracive of the racemic modifications of the compounds of this invention, the diastereomeric mixtures, and pure enantiomers and diastereomers thereof. The utility of a racemic mixture, a diastereomeric mixture as well as of the pure enantiomers and diastereomers is determined by the biological evaluation procedures described below.

Favored because of their greater biological activity relative to that of other compounds described herein are the compounds of formula I wherein A and B together are oxo; A and B when taken individually are hydrogen and hydroxy, respectively; $R_2$ is hydrogen, $R_1$ is hydrogen or alkanoyl; $R_3$ is hydrogen or hydroxymethyl; and Z and W have the values shown below:

| Z | m | n | W |
|---|---|---|---|
| alkylene having from 7 to 11 carbon atoms | — | — | H |
| alkylene having from 4 to 7 carbon atoms | — | — | –⬡–$W_1$, pyridyl |
| $(alk_1)_m$—O—$(alk_2)_n$ | 0,1 | 1 | –⬡–$W_1$, pyridyl | each of $(alk_1)$ and $(alk_2)$ is alkylene having from one to seven carbon atoms with the proviso the summation of carbon atoms in $(alk_1)$ plus $(alk_2)$ is not less than four or greater than seven;

| $(alk_1)_m$—O—$(alk_2)_n$ | 0,1 | 1 | H |
|---|---|---|---| each of $(alk_1)$ and $(alk_2)$ is alkylene having from one to eleven carbon carbon atoms with the proviso the summation of carbon atoms in $(alk_1)$ plus $(alk_2)$ is not less than seven or greater than eleven.

Preferred compounds of formula I are those compounds of formula I wherein
  each of $R_1$ and $R_2$ is hydrogen;
  Z is —$C(CH_3)_2(CH_2)_6$ and W is hydrogen;
  Z is $C_{4-7}$ alkylene and W is phenyl;
  Z is —O—alkylene having 7 to 9 carbon atoms and W is hydrogen;
  Z is —O—alkylene having from 4 to 5 carbon atoms and W is phenyl;
  A is hydrogen and B is hydroxy (cis- and trans-forms);
  A and B taken together are oxo;
  $R_3$=hydroxy or hydroxymethyl.

Especially preferred are the compounds of formula I wherein $R_1$, $R_2$, $R_3$, Z and W are as defined for the preferred compounds, A and B taken individually are hydrogen and hydroxy, respectively and which have formula I′

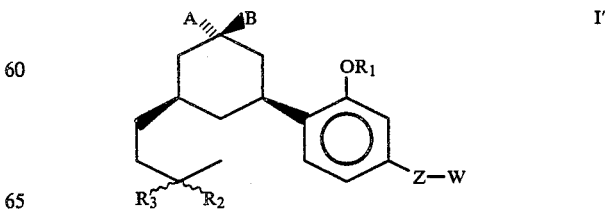

Additionally, the favored and preferred intermediates of formulae II–IV are those compounds having said formulae which serve as intermediates for the favored and preferred compounds of formula I.

DETAILED DESCRIPTION OF THE INVENTION

The compounds of this invention having formula I are prepared by Grignard reaction of the appropriate 2-bromo-5-(Z-W-substituted)phenol, the hydroxy group of which is protected, with the appropriate hexahydronaphthalen-2(1H)-one of formula IV. The reaction is stereoselective and is illustrated in the following reaction sequence by the conversion of a compound of formula IV-A (formula IV wherein $R_2+R_3$=ethylenedioxy) to a compound of formula I-A. Preparation of 2-bromo-5-(Z-W-substituted)phenol reactants is described in U.S. Pat. No. 4,147,872, issued Apr. 3, 1979.

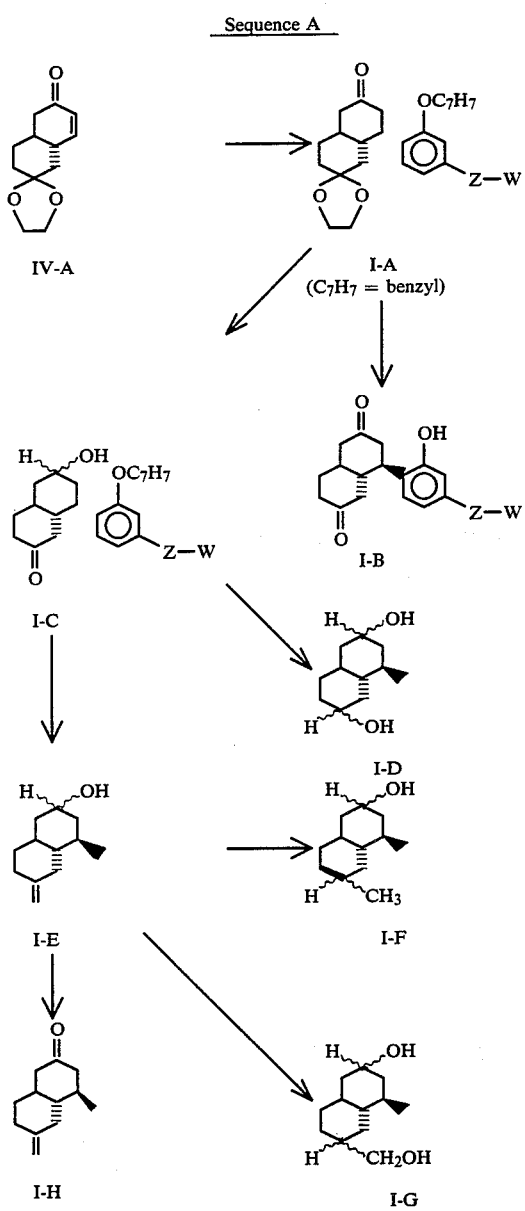

Sequence A

Suitable protecting groups are those which do not interfere with subsequent reactions and which can be removed under conditions which do not cause undesired reactions at other sites of said compounds or of products produced therefrom. Representative of such protective groups are methyl, ethyl and preferably benzyl or substituted benzyl wherein the substituent is, for example, alkyl having from one to four carbon atoms, halo (Cl, Br, F, I) and alkoxy having from one to four carbon atoms; and dimethyl-t-butylsilyl. The ether protecting, or blocking, groups can be removed through the use of hydrobromic acid in acetic acid or hydrobromic acid, 48% aqueous. The reaction is conducted at elevated temperatures and desirably at the reflux temperature. However, when Z is —(alk$_1$)$_m$—O—(alk$_2$)$_m$—, acids such as polyphosphoric acid or trifluoroacetic acid should be used to avoid cleavage of the ether linkage. Other reagents such as hydriodic acid, pyridine hydrochloride or hydrobromide, or lithio n-alkyl mercaptides in hexamethylphosphoramide can be used to remove protecting ether groups such as methyl or ethyl groups. When the protecting groups are benzyl or substituted benzyl groups, they can be removed by catalytic hydrogenolysis. Suitable catalysts are palladium or platinum, especially when supported on carbon. Alternatively they can be removed by solvolysis using trifluoroacetic acid. A further procedure for removing benzyl comprises treatment with n-butyllithium in a reaction-inert solvent at room temperature. The dimethyl-t-butylsilyl group is removed by mild hydrolysis.

The exact chemical structure of the protecting group is not critical to this invention since its importance resides in its ability to perform in the manner described above. The selection and identification of appropriate protecting groups can easily and readily be made by one skilled in the art. The suitability and effectiveness of a group as a hydroxy protecting group are determined by employing such a group in the herein-illustrated reaction sequences. It should, therefore, be a group which is easily removed to regenerate the hydroxy groups. Methyl and benzyl are favored protecting groups since they are readily removed.

The protected 2-bromo-5-(Z-W substituted)phenol is then reacted with magnesium in a reaction-inert solvent and generally in the presence of a promoter, e.g., cuprous salts such as the chloride, bromide and iodide (to promote 1,4-addition) with an appropriate compound of formula IV. Suitable reaction-inert solvents are cyclic and acyclic ethers such as, for example, tetrahydrofuran, dioxane and dimethyl ether of ethylene glycol (diglyme). The Grignard reagent is formed in known manner, as, for example, by refluxing a mixture of one molar proportion of the bromo reactant and two molar proportions of magnesium in a reaction-inert solvent, e.g. tetrahydrofuran. The resulting mixture is then cooled to about 0° C. to −20° C., and cuprous iodide added followed by the appropriate formula IV compound at a temperature of from about 0° C. to −20° C. The amount of cuprous iodide used is not critical but can vary widely. Molar proportions ranging from about 0.2 to about 0.02 moles per mole of bromo reactant afford satisfactory yields of compounds of formula I wherein the phenolic hydroxy group is protected (formula I, $R_1$=a protecting group; A+B=oxo, remaining groups as defined above).

The protected formula I compound is then treated with an appropriate reagent, if desired, to remove the protecting group. The benzyl group is conveniently removed by methods described above. If the protecting group is an alkyl group (methyl or ethyl) it is removed by the above-mentioned methods or by treatment with, for example, pyridine hydrochloride. The ketal group of formula I-A compounds is restored to oxo, if desired, by treatment with acid to provide a compound of formula I-B.

However, in most instances in the processes for preparing compounds of formula I, the protecting groups are retained throughout the overall process and not removed until the penultimate or ultimate process step is reached.

The compounds having formula I-C are prepared from the corresponding protected compounds of formula I-A by reduction. Sodium borohydride is favored as reducing agent in this step since it not only affords satisfactory yields of the desired product, but retains the protecting group on the phenolic hydroxy group, and reacts slowly enough with hydroxylic solvents (methanol, ethanol, water) to permit their use as solvents. Temperatures of from about −40° C. to about 30° C. are generally used. Lower temperatures, even down to −70° C., can be used to increase selectivity of the reduction. Higher temperatures cause reaction of the sodium borohydride with the hydroxylic solvent. If higher temperatures are desired, or required for a given reduction, isopropyl alcohol or the dimethyl ether of diethylene glycol are used as solvents. Sometimes favored as reducing agent is potassium tri-sec-butyl borohydride since it favors stereoselective formation of the 2-beta-hydroxy derivative. The reduction is conducted in dry tetrahydrofuran at a temperature below about −50° C. using equimolar quantities of the ketone compound and reducing agent.

Reducing agents such as lithium borohydride, diisobutylaluminum hydride or lithium aluminum hydride which can also be used require anhydrous conditions and non-hydroxylic solvents, such as 1,2-dimethoxyethane, tetrahydrofuran, diethyl ether, dimethyl ether of diethylene glycol.

The deprotected compounds of formula I, except those of formulae I-E, wherein A is hydrogen and each of B and $OR_1$ is hydroxy can, of course, be obtained directly by catalytic reduction of the corresponding protected compounds (formula I, A+B=oxo, $R_1$=benzyl) over palladium-on-carbon, or by chemical reduction of the unprotected compounds (formula I, A+B=oxo, $R_1$=H) using the reducing agents described above. In practice it is preferred to produce the deprotected compounds of formula I (A=H, B=OH) by reduction of the corresponding benzyl protected compounds of formula I (A+B=oxo, $R_1$=benzyl) as described above since it permits stereochemical control of the reduction and formation of the 2-beta hydroxy epimer (see conversion I-A to I-C) as the major product and thus facilitates separation and purification of the epimeric 2-hydroxy derivatives. The ketal group at the 6-position, if present, is converted to oxo by treatment with aqueous acid. Debenzylation of formulae I-E compounds is accomplished by reaction with n-butyllithium in hexane in order to avoid reduction of the 6-methylene group.

Compounds of formula I-C serve as intermediates for compounds of formula I-D through I-G. Reduction of the oxo group by methods such as those described above affords the corresponding dihydroxy compound I-D.

Compounds of this invention wherein $R_2$ and $R_3$ taken together are methylene (I-E) are readily prepared from the corresponding oxo compounds (I-C) via the Wittig reaction with methylene triphenylphosphorane or other appropriate methylide. The usual procedure comprises generating the Wittig reagent; that is, the methylide, in situ and, immediately following generation of the methylide, reacting it with the appropriate oxo compound. A convenient procedure for generating the methylide comprises reacting sodium hydride with dimethyl sulfoxide (sodium dimsyl) at a temperature of from about 50° C.-80° C., usually until evolution of hydrogen ceases, followed by reacting the resulting solution with methyl triphenyl phosphonium bromide at a temperature of from about 10° C. to about 80° C. To the thus-produced solution of the ylide is then added the appropriate oxo compound and the mixture stirred at temperatures ranging from about room temperature to 80° C. The methylene compound thus produced is isolated by known procedures.

Other methods of generating the methylide are, of course, known and can be used in lieu of the above-described procedure. Typical procedures are described by Maercker, *Organic Reactions,* 14, 270 (1965). In the oxo compounds having formula I-C, the phenolic hydroxy group can be protected by groups other than benzyl if desired as, for example, by conversion to an alkanoyloxy derivative or to an ether such as, for example, a tetrahydropyranyl ether. However, protection of the phenolic hydroxy group is not absolutely necessary if sufficient base is present to convert the phenolic hydroxy group to an alkoxide.

The methylene derivatives of formula I-E are reduced to corresponding methyl derivatives (I-F) by catalytic hydrogenation. Simultaneous removal of the benzyl protecting group also occurs.

Conversion of the methylene derivatives (I-E) to hydroxymethyl derivatives (I-G) is accomplished by hydroboration-oxidation. Borane in tetrahydrofuran is favored for the hydroboration step since it is commercially available and gives satisfactory yields of the desired hydroxymethyl compound. The reaction is generally conducted in tetrahydrofuran or diethylene glycol dimethyl ether (diglyme). The borane product is not isolated but is directly oxidized with alkaline hydrogen peroxide to the hydroxymethyl compound.

Compounds of formulae I-D, I-F and I-G wherein the 2-hydroxy group and the $R_3$ substituent (OH, $CH_3$, $CH_2OH$) have the beta configuration are resolved into their diastereomers by formation of the corresponding d-mandelates by reaction with d-mandelic acid. When $R_3$ is OH or $CH_2OH$, the bis-d-mandelate derivative is formed. A convenient method of preparing the d-mandelates comprises reacting said formulae I-D, I-F and I-G compounds with an excess of d-mandelic acid in benzene in the presence of p-toluenesulfonic acid monohydrate at the reflux with continuous removal of water. The diastereomeric mandelates thus prepared are separated via column chromatography on silica gel. Hydrolysis of the esters using potassium carbonate in methanol-tetrahydrofuran-water affords the enantiomeric I-D, I-F and I-G compounds.

Esters of formula I compounds wherein only group $OR_1$ is acylated are prepared by reacting formula I compounds wherein A together with B represent oxo and $R_3$ is other than hydroxy or hydroxymethyl with the appropriate alkanoic acid or acid of formula HOO-C—$(CH_2)_p$—$NR_2R_3$ in the presence of a condensing agent such as dicyclohexylcarbodiimide followed by reduction of the oxo group to OH. Alternatively, they are prepared by reaction of a formula I compound with the appropriate alkanoic acid chloride or anhydride, e.g., acetyl chloride or acetic anhydride, in the presence of a base such as pyridine. The monoacylated product is then subjected to further reactions, if desirable, such as reduction of A+B=oxo to the corresponding alcohol.

Diesters of formula I compounds in which each of B and $OR_1$ groups is hydroxy and $R_3$ is other than hydroxy or hydroxymethyl are prepared by acylation according to the above-described procedures. Compounds in which only the B-hydroxy group is acylated are obtained by mild hydrolysis of the corresponding diacyl derivative, advantage being taken of the greater ease of hydrolysis of the phenolic acyl group. Formula I compounds in which only the phenolic hydroxy group is esterified are obtained by borohydride reduction of the corresponding formula I ketone (A+B=oxo) which is esterified at the phenolic hydroxy group. The thus-produced formula I compounds in which only one OH group is acylated can then be acylated further with a different acylating agent to produce a diesterified compound of formula I in which the ester groups represented by B and $OR_1$ are different.

Diesters of compounds wherein each of $OR_1$ and B is hydroxy and $R_3$ is hydroxy or hydroxymethyl are also prepared by acylation of the appropriate trihydroxy containing derivative with at least three equivalents of an appropriate acylating agent, e.g., acid chloride, acid anhydride or acid plus condensing agent, as described above. The order of acylation of the hydroxy groups appears to be $R_3(=CH_2OH) > OR_1 > B$. This observation permits acylation of $R_3$ in the presence of $OR_1$ and B as OH. Diesters of formula I compounds in which each of $OR_1$ and $R_3$ is alkanoyloxy are prepared by acylating the appropriate formula I compound wherein A+B is oxo and each of $OR_1$ and $R_3$ is hydroxy. The oxo (A+B) group is then reduced, if desired, by means of sodium borohydride. The hydroxy group thus produced can be acylated with a different acylating agent to produce a mixed ester containing product. Similarly, diesters of formula I compounds wherein each of $OR_1$, B is alkanoyloxy and $R_3$ is hydroxy are obtained by acylation of formula I compounds wherein $R_2+R_3$ is HO and each of $OR_1$ and B is hydroxy. Borohydride reduction of $R_2+R_3$ as oxo affords the desired diesters.

Acylation of a formula I compound wherein $OR_1$ and B is hydroxy and $R_3$ is OH or —$CH_2OH$ with one equivalent of an acylating agent affords a mixture of esters wherein $OR_1$ and/or $R_3$ are acylated. The products are separated chromatographically on silica gel.

Pharmaceutically acceptable acid addition salts of compounds of this invention are readily prepared by well known procedures. A typical procedure comprises reacting the appropriate formula I compound and appropriate acid, generally in stoichiometric amounts, in a reaction-inert solvent, e.g. methanol, and recovering the resulting salt by a suitable method, e.g., filtration, precipitation by addition of a non-solvent such as ether, or evaporation of the solvent. When more than one basic group is present, diacid salt formation becomes possible.

In the above sequence the oxo (or alkylenedioxy) group can be converted to other values of $R_2$ and $R_3$ as defined herein at any step of the sequence if desired. It is generally advantageous for reasons of economy to carry out the sequence as illustrated and to convert the alkylenedioxy group to other values of $R_2$ and $R_3$ as shown in Sequence A.

The required compound of formula IV-A is prepared according to the following reaction sequence.

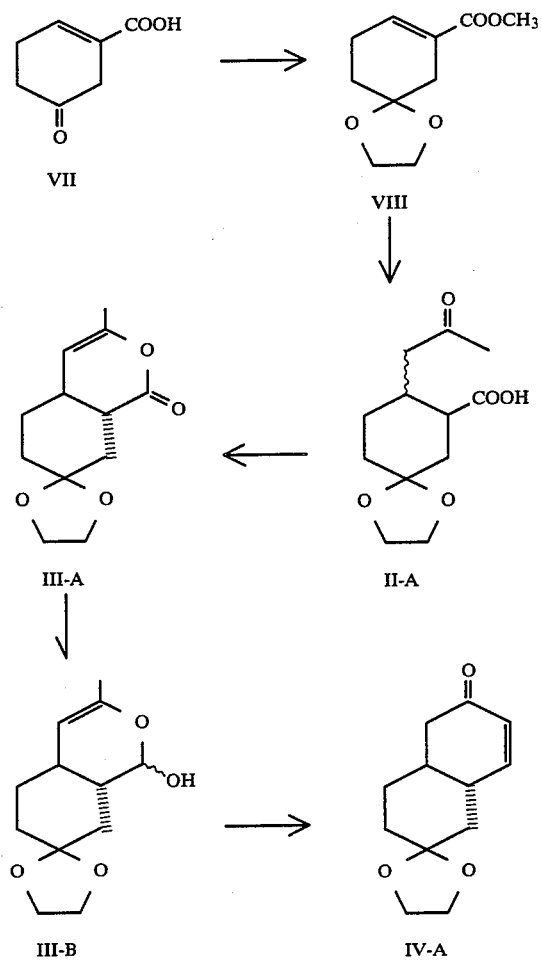

Sequence B:

In this sequence an appropriate 3-carboxycyclohex-3-enone is ketalized using an alkyleneglycol having from two to four carbon atoms according to procedures described above. The ketalized product is then esterified under non-acid conditions such as by using dimethyl sulfate in the presence of potassium carbonate. The unsaturated ester (VIII) is then converted to ketone II-A by reaction with metallated acetone dimethylhydrazone. The reaction comprises metallating the dimethylhydrazone of acetone by reaction with a suitable lithiating agent such as n-butyllithium or lithium diisopropylamide in a reaction-inert solvent such as tetrahydrofuran at 0° C. or lower. The lithiated acetone dimethylhydrazone is then reacted with a solution of cuprous iodide-diisopropylsulfide in tetrahydrofuran or other reaction-inert solvent at a temperature of −78° C. to −50° C. The temperature of the reaction mixture is gradually warmed to about 0° C. over a period of one half to one hour and then cooled to about −78° C. The cuprate thus prepared is then reacted with the unsaturated ester VIII to produce the dimethylhydrazone of the ester of II-A. Oxidative hydrolysis of the dimethylhydrazone using, for example, aqueous sodium periodate at pH 7, or by means of cupric chloride in water-tetrahydrofuran at pH 7 affords the ester of II-A. Hydrolysis (saponification) of the ester provides II-A.

Ketone II-A is transformed to the enolic lactone III-A by treatment with sodium acetate in acetic anhydride at an elevated temperature, e.g., reflux. Other dehydrating conditions can, of course, be used.

The enol lactone is then treated with diisobutylaluminum hydride in a reaction-inert solvent at a temperature of −20° C. or lower. Other useful reducing agents are lithium tri-sec-butyl hydride, 9-borobicyclo[3.3.1]nanone, and lithium tri-tert-butoxyaluminohydride. The keto aldehyde thus produced, and which is in equilibrium with the corresponding lactol (III-B) is then cyclized by intramolecular aldol condensation using a secondary amine, preferably pyrrolidine, and acetic acid as catalysts to provide the bicyclic ketone (IV-A).

Alternatively, the compound of formula IV-A is preferably produced by reaction of decahydro-2,6-naphthalenedione monoethylene ketal with lithium diisopropylamide in a reaction-inert solvent, e.g. tetrahydrofuran, at an initial temperature of about −50° C. to −78° C. followed by warming to ambient temperature. The mixture is then cooled to −10° C. to +10° C. and treated with diphenyldisulfide. Oxidation of the 3-alpha-phenylthiodecahydro-2,6-naphthalenedione 6-monoethylene ketal thus produced with a peracid such as m-chloro-peroxybenzoic acid at 0° C. to 20° C. in a reaction-inert solvent ($CH_2Cl_2$) affords the corresponding phenylsulfenyl derivative. Said compound can be produced in a single step by reacting decahydro-2,6-naphthalenedione monoethylene ketal with an alkylphenylsulfinate in the presence of an alkali metal hydride at about 0° C. in diglyme.

Treatment of the phenylsulfinyl derivative with a solid base ($CaCO_3$) in toluene at 110° C. produces the compound of formula IV-A.

Also of value as CNS agents, anticonvulsants, antiemetics, analgesics and antidiarrheal agents in the same manner as compounds of formula I above, are compounds of formula I wherein A is hydrogen and B is hydrogen, amino or acetamido; and $R_1$, $R_2$, $R_3$, Z and W are as defined in formula I above.

Compounds of this invention wherein B is amino are prepared from the corresponding compounds wherein A and B taken together represent oxo. One procedure comprises converting the appropriate oxo compound (ketone) of formula I to the corresponding oxime or oxime derivative; e.g., an alkyl ether or an acetyl derivative, followed by reduction of the oxime or derivative thereof to the desired amine. Of course, when $R_2$ and $R_3$ taken together represent oxo, said oxo group must be protected to avoid reaction at that site. The ketal ($R_2+R_3$=alkylenedioxy) group is a preferred protecting group because of the ease of preparation of said compounds and the relative ease of removal of said group to regenerate the oxo group.

The oximes of compounds of formula I wherein A and B taken together represent oxo, and $R_2$ and $R_3$ taken together are other than oxo, are prepared by reacting said compounds with hydroxylamine hydrochloride in a solution of methanol-water at room temperature. In practice, it is preferred to use an excess of hydroxylamine, up to as much as a three fold excess. Under such conditions the preparation of the desired oxime derivative is complete in 1 to 2 hours. The product is isolated by addition of the reaction mixture to water followed by basification to pH 9.5 and extraction with a water-immiscible solvent such as ethyl acetate.

When O-methylhydroxylamine hydrochloride is employed in place of hydroxylamine hydrochloride, the reaction provides the O-methyloxime derivative. When using O-methylhydroxylamine, it is preferred to extend the reaction time to 6 to 12 hours. Isolation of the product is carried out in the same manner as previously described for the oxime derivative.

Preparation of the O-acetyloxime compounds is accomplished by acetylation of the corresponding oxime with an equimolar amount of acetic anhydride in the presence of an equimolar amount of pyridine. The use of an excess of the anhydride and pyridine aid in the completion of the reaction and an excess of two to three fold of each is preferred. The reaction is best conduced in an aprotic hydrocarbon solvent such as benzene or toluene at room temperature overnight. On completion of the reaction, water is added and the product is separated in the hydrocarbon layer. Alternatively, O-acetyl derivatives can be prepared by treating the requisite oxo compound with O-acetylhydroxylamine hydrochloride under reaction conditions similar to those described above for preparation of the oxime derivatives.

The oxime or oxime derivative is then reduced catalytically using, for example, Raney nickel, palladium-on-charcoal or platinum oxide at an initial hydrogen pressure of about 2–3 atmospheres at ambient temperature in a reaction-inert solvent such as $C_{1-4}$ alkanol, or lithium aluminum hydride in a reaction-inert solvent such as tetrahydrofuran at reflux temperature.

A still further procedure comprises the Gabriel synthesis in which potassium phthalimide is reacted with a 4-halo, e.g. 4-iodo- or 4-bromo derivative of a compound of formula I (B=I, Br) and the resulting phthalimide derivative hydrolyzed with a base such as sodium or potassium hydroxide or hydrazine. The 4-halo compound of formula I is prepared by reaction of the corresponding hydroxy compound of formula I-C with phosphorous halide or hydrogen halide.

A favored procedure for preparing amino compounds of formula I comprises condensation of the appropriate formula I compound wherein A and B taken together represent oxo with the ammonium salt of a lower alkanoic acid and subsequent reduction of the in situ generated imine. In addition to lower alkanoic acid ammonium salts, ammonium salts of inorganic acids can also be used in this procedure.

A further favored procedure comprises reaction of the appropriate compound of formula I wherein B is alpha-hydroxy with equimolar quantities of phthalimide, triphenylphosphine and diethylazodicarboxylate.

In practice, a solution of the ketone (A+B=O) in a lower alkanol such as methanol is treated with an ammonium salt of an alkanoic acid such as acetic acid and the cooled reaction mixture treated with the reducing agent sodium cyanoborohydride. The reaction is allowed to proceed at room temperature for several hours, and is subsequently hydrolyzed and the product isolated.

Although stoichiometric proportions of ketone and ammonium alkanoate are required, it is advantageous to use up to a ten fold excess of ammonium alkanoate in order to ensure rapid formation of the imine. It is also advantageous to conduct the reduction at ambient temperature and to use two moles of sodium cyanoborohydride per mole of ketone reactant in order to maximize yield of the final product. Reaction is complete in 2–3 hours.

Reduction of the imine can, of course, be carried out with other reducing agents such as palladium-on-charcoal. In practice, a solution of the appropriate ketone in a lower alkanol, such as methanol or isopropanol, is treated with an ammonium alkanoate, such as ammonium acetate, and 10% palladium-on-charcoal, and the resulting suspension shaken in a hydrogen atmosphere at temperatures of about 25°–50° C. until the theoretical amount of hydrogen has been absorbed. It is preferred that a 10 fold excess of the ammonium alkanoate be employed to ensure complete reaction in a reasonable time period. The amount of the catalyst can vary from 10% to 50% on a weight basis, of the starting ketone. The initial pressure of the hydrogen is not critical, and a pressure from one to fifty atmospheres is preferred to shorten the reaction time. Employing the aforementioned parameters, the reaction time will vary between 2 to 6 hours. Upon completion of the reductive amination reaction, the spent catalyst is filtered and the filtrate concentrated to dryness.

The amino compounds produced by the above procedures are isolated by taking advantage of their basic nature which permits convenient separation from non-basic by-products and reactants. In general, an aqueous solution of the product is extracted over a range of gradually increasing pH so that non-basic materials are removed at the lower pH's and the product at a pH of about 9. The extracting solvents, e.g. ethyl acetate, diethyl ether, are back-washed with brine and water, dried and evaporated to give the product.

Formula I compounds wherein each of A and B is hydrogen are prepared from corresponding compounds wherein A and B taken together are oxo. The process comprises converting the oxo group to a hydrazone (or semicarbazone) and then decomposing said hydrazone (or semicarbazone) by alkali such as sodium or potassium hydroxide to produce the desired compound wherein each of A and B is hydrogen. The process is readily carried out by heating a mixture of the appropriate compound of formula I wherein A and B taken together are oxo and $R_2$ and $R_3$ taken together are other than oxo with hydrazine hydrate in a reaction inert solvent such as ethylene glycol or triethylene glycol at 100° C. Solid potassium (or sodium) hydroxide is then added and the mixture heated at an elevated temperature, e.g. 150°–200° C. It is then cooled, acidified and the product recovered, e.g. by extraction with ether, or other known method.

Esters of formula I compounds in which the amino group and/or hydroxy groups ($OR_1$, B, $R_3$) are acylated are prepared by acylation with the appropriate alkanoic acid or amino acid in the presence of a condensing agent such as dicyclohexylcarbodiimide or by reaction with the appropriate alkanoic acid chloride or anhydride, e.g. acetyl chloride or acetic anhydride, in the presence of a base such as pyridine.

When B is amino, further opportunity for formation of pharmaceutically acceptable acid addition salts exists and, when more than one basic group is present, to formation of poly-acid addition salts according to procedures described herein.

The analgesic properties of the compounds of this invention are determined by tests using nociceptive stimuli.

TESTS USING THERMAL NOCICEPTIVE STIMULI (a) Mouse Hot Plate Analgesic Testing The method used is modified after Woolfe and MacDonald, *J. Pharmacol. Exp. Ther.*, 80, 300–307 (1944). A controlled heat stimulus is applied to the feet of mice on a ⅛-inch thick aluminum plate. A 250 watt reflector infrared heat lamp is placed under the bottom of the aluminum plate. A thermal regulator, connected to thermistors on the plate surface, programs the heat lamp to maintain a constant temperature of 57° C. Each mouse is dropped into a glass cylinder (6½-inch diameter) resting on the hot plate, and timing is begun when the animal's feet touch the plate. The mouse is observed at 0.5 and 2 hours after treatment with the test compound for the first "flicking" movements of one or both hind feet, or until 10 seconds elapse without such movements. Morphine has an $MPE_{50}=4–5.6$ mg./kg. (s.c.).

(b) Mouse Tail Flick Analgesic Testing

Tail flick testing in mice is modified after D'Amour and Smith, *J. Pharmacol. Exp. Ther.*, 72, 74–79 (1941) using controlled high intensity heat applied to the tail. Each mouse is placed in a snug-fitting metal cylinder, with the tail protruding through one end. This cylinder is arranged so that the tail lies flat over a concealed heat lamp. At the onset of testing an aluminum flag over the lamp is drawn back, allowing the light beam to pass through the slit and focus onto the end of the tail. A timer is simultaneously activated. The latency of a sudden flick of the tail is ascertained. Untreated mice usually react within 3–4 seconds after exposure to the lamp. The end point for protection is 10 seconds. Each mouse is tested at 0.5 and 2 hours after treatment with morphine and the test compound. Morphine has an $MPE_{50}$ of 3.2–5.6 mg./kg. (s.c.).

(c) Tail Immersion Procedure

The method is a modification of the receptacle procedure developed by Benbasset, et al., *Arch. int. Pharmacodyn.*, 122, 434 (1959). Male albino mice (19–21 g.) of the Charles River CD-1 strain are weighed and marked for identification. Five animals are normally used in each drug treatment group with each animal serving as its own control. For general screening purposes, new test agents are first administered at a dose of 56 mg./kg. intraperitoneally or subcutaneously, delivered in a volume of 10 ml./kg. Preceding drug treatment and at 0.5 and 2 hours post drug, each animal is placed in the cylinder. Each cylinder is provided with holes to allow for adequate ventilation and is closed by a round nylon plug through which the animal's tail protrudes. The cylinder is held in an upright position and the tail is completely immersed in the constant temperature waterbath (56° C.). The endpoint for each trial is an energetic jerk or twitch of the tail coupled with a motor response. In some cases, the endpoint may be less vigorous post drug. To prevent undue tissue damage, the trial is terminated and the tail removed from the waterbath within 10 seconds. The response latency is recorded in seconds to the nearest 0.5 second. A vehicle control and a standard of known potency are tested concurrently with screening candidates. If the activity of a test agent has not returned to baseline values at the 2-hour testing point, response latencies are determined at 4 and 6 hours. A final measurement is made at 24 hours if activity is still observed at the end of the test day.

TEST USING CHEMICAL NOCICEPTIVE STIMULI

Suppression of Phenylbenzoquinone Irritant-Induced Writhing

Groups of 5 Carworth Farms CF-1 mice are pretreated subcutaneously or orally with saline, morphine, codeine or the test compound. Twenty minutes (if treated subcutaneously) or fifty minutes (if treated orally) later, each group is treated with intraperitoneal injection of phenylbenzoquinone, an irritant known to produce abdominal contractions. The mice are observed for 5 minutes for the presence or absence of writhing started 5 minutes after the injection of the irritant. $MPE_{50}$'s of the drug pretreatments in blocking writhing are ascertained.

TESTS USING PRESSURE NOCICEPTIVE STIMULI

Effect on the Haffner Tail Pinch Procedure

A modification of the procedure of Haffner, *Experimentelle Prufung Schmerzstillender. Deutch Med. Wschr.*, 55, 731–732 (1929) is used to ascertain the effects of the test compound on aggressive attacking responses elicited by a stimulus pinching the tail. Male albino rats (50–60 g.) of the Charles River (Sprague-Dawley) CD strain are used. Prior to drug treatment, and again at 0.5, 1, 2 and 3 hours after treatment, a Johns Hopkins 2.5-inch "bulldog" clamp is clamped onto the root of the rat's tail. The end-point at each trial is clear attacking and biting behavior directed toward the offending stimulus, with the latency for attack recorded in seconds. The clamp is removed in 30 seconds if attacking has not yet occurred, and the latency of response is recorded as 30 seconds. Morphine is active at 17.8 mg./kg. (i.p.).

TESTS USING ELECTRICAL NOCICEPTIVE STIMULI

The "Flinch-Jump" Test

A modification of the flinch-jump procedure of Tenen, *Psychopharmacologia*, 12, 278–285 (1968) is used for determining pain thresholds. Male albino rats (175–200 g.) of the Charles River (Sprague-Dawley) CD strain are used. Prior to receiving the drug, the feet of each rat are dipped into a 20% glycerol/saline solution. The animals are then placed in a chamber and presented with a series of 1-second shocks to the feet which are delivered in increasing intensity at 30-second intervals. These intensities are 0.26, 0.39, 0.52, 0.78, 1.05, 1.31, 1.58, 1.86, 2.13, 2.42, 2.72 and 3.04 mA. Each animals's behavior is rated for the presence of (a) flinch, (b) squeak and (c) jump or rapid forward movement at shock onset. Single upward series of shock intensities are presented to each rat just prior to, and at 0.5, 2, 4 and 24 hours subsequent to drug treatment.

Results of the above tests are recorded as percent maximum possible effect (%MPE). The %MPE of each group is statistically compared to the %MPE of the standard and the predrug control values. The %MPE is calculated as follows:

$$\% \text{ MPE} = \frac{\text{test time} - \text{control time}}{\text{cutoff time} - \text{control time}} \times 100$$

The compounds of this invention, when used as analgesics via oral or parenteral administration, are conveniently administered in composition form. Such compositions include a pharmaceutical carrier selected on the basis of the chosen route of administration and standard pharmaceutical practics. For example, they can be administered in the form of tablets, pills, powders or granules containing such excipients as starch, milk sugar, certain types of clay, etc. They can be administered in capsules, in admixtures with the same or equivalent excipients. They can also be administered in the form of oral suspensions, solutions, emulsions, syrups and elixirs which may contain flavoring and coloring agents. For oral administration of the therapeutic agents of this invention, tablets or capsules containing from about 0.01 to about 100 mg. are suitable for most applications.

The physician will determine the dosage which will be most suitable for an individual patient and it will vary with the age, weight and response of the particular patient and the route of administration. Generally, however, the initial analgesic dosage in adults may range from about 0.1 to about 750 mg. per day in single or divided doses. In many instances, it is not necessary to exceed 100 mg. daily. The favored oral dosage range is from about 1.0 to about 300 mg./day; the preferred dose is from about 1.0 to about 50 mg./day. The favored parenteral dose is from about 0.1 to about 100 mg./day; the preferred range from about 0.1 to about 20 mg./day.

This invention also provides pharmaceutical compositions, including unit dosage forms, valuable for the use of the herein described compounds as analgesics and other utilities disclosed herein. The dosage form can be given in single or multiple doses, as previously noted, to achieve the daily dosage effective for a particular utility.

The compounds (drugs) described herein can be formulated for administration in solid or liquid form for oral or parenteral administration. Capsules containing drugs of this invention are prepared by mixing one part by weight of drug with nine parts of excipient such as starch or milk sugar and then loading the mixture into telescoping gelatin capsules such that each capsule contains 100 parts of the mixture. Tablets containing said compounds are prepared by compounding suitable mixtures of drug and standard ingredients used in preparing tablets, such as starch, binders and lubricants, such that each tablet contains from 0.10 to 100 mg. of drug per tablet.

Suspensions and solutions of these drugs, particularly those wherein $R_1$ (formula I) is hydroxy, are often prepared just prior to use in order to avoid problems of stability of the suspensions or solution (e.g. precipitation) of the drug upon storage. Compositions suitable for such are generally dry solid compositions which are reconstituted for injectable administration.

By means of the above procedures, the analgesic activity of several compounds of this invention is determined. The compounds have the formula shown below:

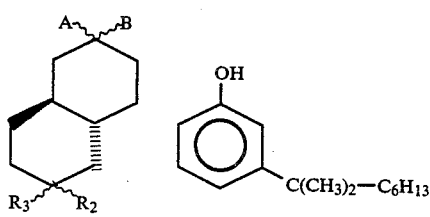

The following abbreviations are used in the Tables: PBQ=phenylbenzoquinone-induced writhing; TF=tail flick; HP=hot plate; RTC=rat tail clamp; and FJ=flinch jump.

TABLE I

| Analgesic Activity - MPE$_{50}$, mg./kg. Route = Subcutaneous. | | | | | |
|---|---|---|---|---|---|
| A | B | $R_2$ | $R_3$ | PBQ | RTC |
| —O— | | H | H | 3.19 | — |
| —H | ◂OH | H | H | 1.46 | 13.4 |
| ◂H | —OH | H | H | 1.24 | — |
| —H | ◂OH | —H | ◂OH | 0.55 | 2.3 |
| —H | ◂OH | ▸H | —OH | 3.22 | 6.9 |
| —H[c] | ◂OH | ▸H | ◂CH$_2$OH | 0.054 | 0.22 |
| —H | ◂OH | ◂H | —CH$_2$OH | 2.81 | 6.8 |
| —H | ◂OH | —O— | | 1.44 | 5.6 |
| —H[a] | ◂OH | —H | ◂CH$_2$OH | 0.018 | 0.06 |
| —H[b] | ◂OH | —H | ◂CH$_2$OH | 1.58 | 10 |

[a] Pure enantiomer A
[b] Pure enantiomer B
[c] Analgesic activity by oral administration: PBQ = 0.25; RTC = 0.7 mg./kg The antiemetic properties of the compounds of formula I are determined in unanesthetized unrestrained cats according to the procedure described in Proc. Soc. Exptl. Biol. and Med., 160, 437–440 (1979).

The compounds of the present invention are active antiemetics via oral and parenteral administration and are conveniently administered in composition form. Such compositions include a pharmaceutical carrier selected on the basis of the chosen route of administration and standard pharmaceutical practice. For example, they may be administered in the form of tablets, pills, powders or granules containing such excipients as starch, milk sugar, certain types of clay, etc. They may be administered in capsules, in admixtures with the same or equivalent excipients. They may also be administered in the form of oral suspensions, dispersions, solutions, emulsions, syrups and elixirs which may containing flavoring and coloring agents. For oral administration of the therapeutic agents of this invention, tablets or capsules containing from about 0.01 to about 100 mg. are suitable for most applications.

The physician will determine the dosage which will be most suitable for an individual patient and it will vary with the age, weight and response of the particular patient and the route of administration. Generally, however, the initial antiemetic dose of drug is administered in an amount effective to prevent nausea. Such dosage in adults may range from 0.01 to 500 mg. per day in single or divided doses. In many instances, it is not necessary to exceed 100 mg. daily. The favored oral dosage range is from about 0.01 to about 300 mg./day; the preferred range is from about 0.10 to about 50 mg./day. The favored parenteral dose is from about 0.01 to about 100 mg./day; the preferred range from about 0.01 to about 20 mg./day.

Their antidiarrheal utility is determined by a modification of the procedure of Neimegeers et al., *Modern Pharmacology-Toxicology*, Willem van Bever and Harbans Lal, Eds., 7, 68–73 (1976). In general, the dosage levels and routes of administration for use of these compounds as antidiarrheal agents parallels those with respect to their use as analgesic agents.

The compounds (drugs) described herein can be formulated for administration in solid or liquid form for oral or parenteral administration. Capsules containing compounds of formulae I or II are prepared by mixing one part by weight of drug with nine parts of excipient such as starch or milk sugar and then loading the mixture into telescoping gelatin capsules such that each capsules contains 100 parts of the mixture. Tablets are prepared by compounding suitable mixtures of drug and standard ingredients used in preparing tablets, such as starch, binders and lubricants, such that each tablet contains from 0.01 to 100 mg. of drug per tablet.

In addition to these uses, the herein-described compounds also exhibit activity as tranquilizers, sedatives, anticonvulsants, diuretics and as antianxiety agents.

EXAMPLE 1

3,4-alpha,4a-beta,5,6,7,8,8a-alpha-Octahydro-4-beta-[2-benzyloxy-4-(1,1-dimethylheptyl)phenyl]-naphthalen-2(1H)-one A solution of 5.20 g. (13.4 mmole) of 1-bromo-2-benzyloxy-4-(1,1-dimethylheptyl)benzene in 27 ml. of tetrahydrofuran is slowly added to 641 mg. (26.7 mmole) of magnesium metal. After a 5 minute initiation period the rate of addition is adjusted such that reflux is just maintained. The reaction mixture is stirred 30 minutes longer while cooling to 25° C. It is then cooled to −15° C. and 127 mg. (0.668 mmole) of cuprous iodide is added. The resultant mixture is stirred 5 minutes and then a solution of 1.8 g. (12.2 mmole) of trans-4a,5,6,7,8,8a-hexahydro-naphthalen-2(1H)-one in 10 ml. of tetrahydrofuran is added over a 10 minute period. Half way through the addition of the naphthalenone another 127 mg. (0.668 mmole) portion of cuprous iodide is added. The reaction mixture is stirred 5 minutes longer and then added to 250 ml. of cold, saturated ammonium chloride and 250 ml. of ether. The ether extract of the quenched reaction is washed once with 250 ml. of saturated ammonium chloride, dried over magnesium sulfate and evaporated to an oil. The crude oil is purified via column chromatography on 150 g. of silica gel eluted with 10 ml. fractions with 15% ether-petroleum ether to yield 3.45 g. (62%) of the title compound as an oil.

IR (CHCl$_3$): 1724, 1626 and 1582 cm$^{-1}$.

MS (m/e): 460 (M⊕), 440, 375, 369, 363, 351 and 91.

PMR (CDCl$_3$): delta 0.88 (m, terminal methyl), 1.28 (s, gem dimethyls), 5.12 (s, benzylic methylene), 6.90 (dd, J=8 and 2 Hz, ArH), 6.90 (d, J=2 Hz, ArH), 7.12 (d, J=8 Hz, ArH) and 7.42 (s, PhH).

In like manner, the following compounds are prepared by substituting equivalent amounts of the appropriate 1-bromo-2-benzyloxy-4(substituted)benzenes for 1-bromo-2-benzyloxy-4-(1,1-dimethylheptyl)benzene.

| Z | W |
|---|---|
| C(CH$_3$)$_2$(CH$_2$)$_4$ | H |
| (CH$_2$)$_8$ | H |
| C(CH$_3$)$_2$(CH$_2$)$_6$ | H |
| (CH$_2$)$_7$ | H |
| C(CH$_3$)$_2$(CH$_2$)$_8$ | H |
| CH(CH$_3$)CH(CH$_3$)(CH$_2$)$_5$ | H |
| (CH$_2$)$_{11}$ | H |
| (CH$_2$)$_3$ | C$_6$H$_5$ |
| CH(CH$_3$)(CH$_2$)$_5$ | C$_6$H$_5$ |

-continued

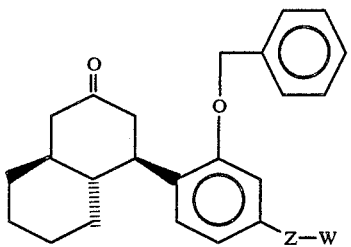

| Z | W |
|---|---|
| CH(CH$_3$)(CH$_2$)$_3$ | C$_6$H$_5$ |
| CH(CH$_3$)CH(CH$_3$)(CH$_2$)$_3$ | C$_6$H$_5$ |
| (CH$_2$)$_8$ | C$_6$H$_5$ |
| CH(CH$_3$)(CH$_2$)$_3$ | 4-FC$_6$H$_4$ |
| CH(C$_2$H$_5$)(CH$_2$)$_4$ | 4-FC$_6$H$_4$ |
| CH(C$_2$H$_5$)(CH$_2$)$_2$ | 4-ClC$_6$H$_4$ |
| (CH$_2$)$_5$ | H |
| (CH$_2$)$_{13}$ | H |
| O(CH$_2$)$_5$ | H |
| O(CH(CH$_3$)CH$_2$ | C$_6$H$_5$ |
| CH(CH$_3$)(CH$_2$)$_3$ | 4-ClC$_6$H$_4$ |
| (CH$_2$)$_4$ | 4-pyridyl |
| CH(CH$_3$)(CH$_2$)$_3$ | 4-pyridyl |
| CH(C$_2$H$_5$)CH$_2$ | 4-pyridyl |
| (CH$_2$)$_7$ | 4-pyridyl |
| CH(CH$_3$)CH(CH$_3$)CH$_2$ | 4-pyridyl |
| CH(CH$_3$)CH(CH$_3$)CH$_2$ | 3-pyridyl |
| CH(CH$_3$)(CH$_2$)$_3$ | 2-pyridyl |
| (CH$_2$)$_3$O(CH$_2$)$_4$ | H |
| (CH$_2$)O(CH$_2$)$_7$ | H |
| C(CH$_3$)$_2$(CH$_2$)$_2$O(CH$_2$)$_2$ | H |
| (CH$_2$)$_7$O | H |
| (CH$_2$)$_{11}$O | H |
| CH(CH$_3$)(CH$_2$)$_6$O | H |
| CH(CH$_3$)CH$_2$O(CH$_2$)$_4$ | C$_6$H$_5$ |
| (CH$_2$)$_3$OCH(CH$_3$) | C$_6$H$_5$ |
| O(CH$_2$)$_7$ | H |
| OCH(CH$_3$)(CH$_2$)$_9$ | H |
| OCH(CH$_3$)(CH$_2$)$_5$ | H |
| OC(CH$_3$)$_2$(CH$_2$)$_5$ | H |
| OC(CH$_3$)$_2$(CH$_2$)$_7$ | H |
| O(CH$_2$)$_2$C(CH$_3$)$_2$(CH$_2$)$_2$ | H |
| O(CH$_2$)$_4$ | C$_6$H$_5$ |
| O(CH$_2$)$_6$ | C$_6$H$_5$ |
| OC(CH$_3$)$_2$(CH$_2$)$_3$ | C$_6$H$_5$ |
| OCH(CH$_3$)(CH$_2$)$_3$ | C$_6$H$_5$ |
| O(CH$_2$)$_4$ | 4F—C$_6$H$_4$ |
| OCH(CH$_3$)(CH$_2$)$_3$ | 4F—C$_6$H$_4$ |
| OCH(CH$_3$)(CH$_2$)$_5$ | 4F—C$_6$H$_4$ |
| O(CH$_2$)$_7$ | 4Cl—C$_6$H$_4$ |
| OCH(C$_2$H$_5$)(CH$_2$)$_3$ | 4Cl—C$_6$H$_4$ |
| O(CH$_2$)$_3$ | C$_6$H$_5$ |
| O(CH$_2$)$_8$ | 4-FC$_6$H$_4$ |
| OC(CH$_3$)$_2$(CH$_2$)$_5$ | 4-ClC$_6$H$_4$ |
| O(CH$_2$)$_{13}$ | H |
| (CH$_2$)$_4$OCH$_2$ | C$_6$H$_5$ |
| (CH$_2$)$_6$O | C$_6$H$_5$ |
| CH(CH$_3$)(CH$_2$)$_2$O | C$_6$H$_5$ |
| CH(CH$_3$)(CH$_2$)$_5$O | C$_6$H$_5$ |
| (CH$_2$)$_6$O | 4-FC$_6$H$_4$ |
| (CH$_2$)$_6$O | 4-ClC$_6$H$_4$ |
| (CH$_2$)$_3$OCH(CH$_3$) | 2-pyridyl |
| (CH$_2$)$_4$O | 4-pyridyl |
| (CH$_2$)$_3$O(CH$_2$)$_4$ | 4-pyridyl |
| CH$_2$CH(CH$_3$)O(CH$_2$)$_2$ | 4-pyridyl |
| O(CH$_2$)$_5$ | 3-pyridyl |
| O(CH$_2$)$_7$ | 2-pyridyl |
| OCH(CH$_3$)(CH$_2$)$_3$ | 2-pyridyl |
| CH$_2$O(CH$_2$)$_5$ | C$_6$H$_5$ |
| CH(CH$_3$)CH$_2$OCH$_2$ | 4-ClC$_6$H$_4$ |
| CH$_2$O(CH$_2$)$_5$ | 4-FC$_6$H$_4$ |

EXAMPLE 2

1,2-alpha,3,4-alpha,4a-beta,5,6,7,8,8a-alpha-Decahydro-4-beta-[2-benzyloxy-4-(1,1-dimethylheptyl)-phenyl]-naphthalen-2-beta-ol and the 2-alpha isomer To a −5° C. solution of 2.40 g. (5.24 mmole) of 3,4-alpha,4-beta,5,6,7,8,8a-alpha-octahydro-4-beta-[2-benzyloxy-4-(1,1-dimethylheptyl)phenyl]-naphthalen-2(1H)-one in 15 ml. methanol and 5 ml. tetrahydrofuran is added 199 mg. (5.24 mmole) of sodium borohydride. The reaction is stirred 30 minutes and then added to 250 ml. saturated sodium chloride and 250 ml. ether. The ether extract is washed once with 250 ml. saturated sodium chloride, dried over magnesium sulfate and evaporated. The crude residue is purified via column chromatography on 100 g. of silica gel eluted in 12 ml. fractions with 2:1 pentane:ether to yield in order of elution 0.572 g. (24%) of the 2-alpha isomer of the title compound and 1.53 g. (64%) of the title compound.

Title Compound:
IR (CHCl$_3$): 3333, 1618 and 1575 cm$^{-1}$.
MS (m/e): 462 (M⊕), 447, 377, 354, 285, 269 and 91.
PMR (CDCl$_3$): delta 0.85 (m, terminal methyl), 1.28 (s, gem dimethyl), 3.0 (bm, benzylic H), 3.75 (bm, carbinol H), 5.07 (s, benzylic methylene), 6.9 (m, ArH) and 7.36 (s, PhH).

2-alpha Isomer of the Title Compound:
IR (CHCl$_3$): 3571, 3425, 1616 and 1575 cm$^{-1}$.
MS (m/e): 462 (M⊕), 377, 354, 285, 269 and 91.
PMR (CDCl$_3$): delta 0.87 (m, terminal methyl), 1.27 (s, gem dimethyl), 4.18 (m, carbinol H), 5.05 (s, benzylic methylene), 6.85 (m, ArH), 7.07 (d, J=8 Hz, ArH) and 7.38 (m, ArH).

The remaining compounds of Example 1 are reduced in like manner to provide compounds having the formula shown below wherein Z and W are as defined in Example 1.

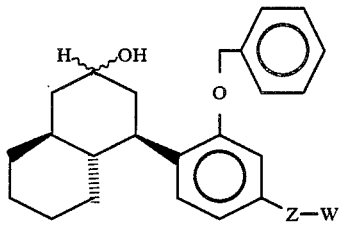

The isomeric alcohols are produced in each instance.

EXAMPLE 3

1,2-alpha,3,4-alpha,4a-beta,5,6,7,8,8a-alpha-Decahydro-4-beta-[4-(1,1-dimethylheptyl)-2-hydroxyphenyl]-naphthalen-2-beta-ol A mixture of 1.48 g. (3.19 mmole) of 1,2-alpha,3,4-alpha,4a-beta,5,6,7,8,8a-alpha-decahydro-4-beta-[2-benzyloxy-4-(1,1-dimethylheptyl)phenyl]-naphthalen-2-beta-ol and 300 mg. of 5% Pd/C/50% H$_2$O in 15 ml. of ethanol is stirred under one atmosphere of hydrogen gas for one hour. The reaction mixture is filtered through diatomaceous earth with ethyl acetate and the filtrate evaporated to an oil. The crude oil is purified via column chromatography on 40 g. of silica gel eluted in 10 ml. fractions with 2:1 pentane:ether to yield 875 mg. (74%) of the title compound.

MP: 127°–8° C. (pentane).

IR (CHCl$_3$): 3333, 1618 and 1582 cm$^{-1}$.

MS (m/e): 372 (M⊕), 354, 287 and 269.

PMR (CDCl$_3$): delta 0.82 (m, terminal methyl), 1.28 (s, gem dimethyl), 2.72 (m, benzylic methine), 3.82 (m, carbinol methine), 6.8 (m, ArH) and 7.08 (d, J=8 Hz, ArH).

Analysis: Calc'd for C$_{25}$H$_{40}$O$_2$: C, 80.59; H, 10.82. Found: C, 80.57; H, 10.62.

Similarly, debenzylation of the remaining betanaphthaleneols of Example 2 according to the above procedure provides the corresponding products having the formula shown below wherein Z and W are as defined in Example 2.

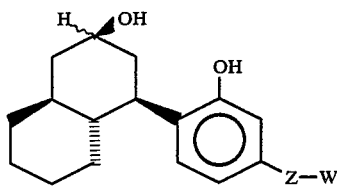

EXAMPLE 4

1,2-beta,3,4-alpha,4a-beta,5,6,7,8,8a-alpha-Decahydro-4-beta-[4-(1,1-dimethylheptyl)-2-hydroxyphenyl]-naphthalen-2-alpha-ol Using the procedure of Example 3, 500 mg. (1.08 mmole) of 1,2-beta,,3,4-alpha,4a-beta,5,6,7,8,8a-alpha-decahydro-4-beta-[2-benzyloxy-4-(1,1-dimethylheptyl)-phenyl]-naphthalen-2-alpha-ol is reduced to give 200 mg. (50%) of the title compound.

MP: 120°-2° C. (pentane).

IR (CHCl$_3$): 3333, 1626 and 1570 cm$^{-1}$.

MS (m/e): 372 (M⊕), 357, 354, 287 and 269.

PMR (CDCl$_3$): delta 0.86 (m, terminal methyl), 1.28 (s, gem dimethyl), 3.00 (m, benzylic methine), 4.28 (m, carbinol methine), 6.84 (m, ArH) and 7.03 (d, J=8 Hz, ArH).

Analysis: Calc'd. for C$_{25}$H$_{40}$O$_2$: C, 89.59; H, 10.82. Found: C, 80.47; H, 10.51.

Debenzylation of the remaining alpha naphthalenols of Example 2 by the above procedure provides the following compounds wherein Z and W are as defined in Example 2.

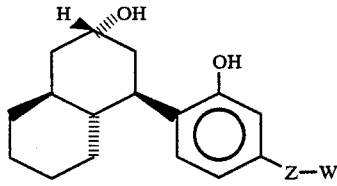

EXAMPLE 5

3,4-alpha,4a-beta,5,6,7,8,8a-alpha-Octahydro-4-beta-[4-(1,1-dimethylheptyl)-2-hydroxyphenyl]-naphthalen-2(1H)-one Using the procedure of Example 3, reduction of 1.00 g. (2.18 mmole) of 3,4-alpha,4a-beta,5,6,7,8,8a-alpha-octahydro-4-beta-[2-benzyloxy-4-(1,1-dimethylheptyl)-phenyl]-naphthalen-2(1H)-one, the title product of Example 1, gives 606 mg. (76%) of the title compound as an oil.

IR (CHCl$_3$): 3571, 3333, 1712, 1626 and 1587 cm$^{-1}$.

MS (m/e): 370 (M⊕), 352, 285 and 273.

PMR (CDCl$_3$): delta 0.82 (terminal methyl), 1.22 (s, gem dimethyl), 5.45 (s, OH), 6.8 (m, ArH) and 7.03 (d, J=8 Hz, ArH).

By means of the above procedure the remaining compounds of Example 1 are reduced to give corresponding compounds of the formula wherein Z and W are as defined in Example 1.

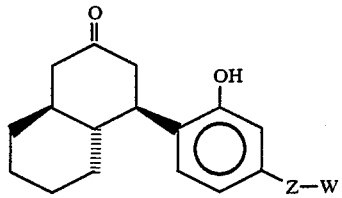

EXAMPLE 6

1,4-Dioxa-7-carboxyspiro[4.5]dec-7-ene

A mixture of 89.8 g. (0.641 mole) of 3-carboxycyclohex-3-enone and 615 mg. (3.17 mmole) of p-toluenesulfonic acid monohydrate in 920 ml. of benzene and 362 ml. of ethylene glycol is heated at reflux with a Dean-Stark trap for 3.5 hours. The cooled reaction mixture is diluted with 1.5 l. water and 3.2 ml. 1N sodium hydroxide. The quenched reaction mixture is then extracted with two 2 l. portions of ether. The combined ether extract is washed with 750 ml. of saturated sodium chloride, dried over magnesium sulfate and evaporated to 91.1 g. of crude oil. The crude product is purified via column chromatography on 1.75 kg. of silica gel eluted with 30% ether-dichloromethane to give the title compound. Crystallization of the title compound from diisopropyl ether gives 49.2 g. (42%) of the title compound.

MP: 72°-3° C. (diisopropyl ether).

IR (CCl$_4$): 2874, 2817, 1678 and 1637 cm$^{-1}$.

MS (m/e): 184 (M⊕), 169, 139 and 86.

PMR (CDCl$_3$): delta 1.8 (bt, methylene), 2.3–2.7 (bm, methylenes), 4.0 (s, ethylene), 7.0–7.2 (bm, olefinic H) and 10.8 (bs, COOH).

Analysis: Calc'd. for C$_9$H$_{12}$O$_4$: C, 58.70; H, 6.57. Found: C, 58.39; H, 6.50.

Repetition of the above procedure but replacing ethylene glycol with an equivalent amount of 1,3-butylene glycol affords the corresponding 1,5-dioxa-8-carboxy-2-methylspiro[5.5]undec-8-ene.

EXAMPLE 7

1,4-Dioxa-7-carbomethoxyspiro[4.5]dec-7-ene

To a refluxing slurry of 66 g. (0.523 mole) of powdered potassium carbonate in 450 ml. of acetone are added simultaneously a solution of 83.0 g. (0.45 mole) of 1,4-dioxa-7-carboxyspiro[4.5]dec-7-ene in 450 ml. of acetone and a solution of 56.8 g. (0.45 mole) of dimethylsulfate in 450 ml. of acetone. The reaction mixture is refluxed 45 minutes longer and then filtered. The filtrate is evaporated to yield the crude title compound. Distillation of the crude product yields 87.7 g. (98%) of the title compound.

BP: 95° C. (2 torr).

IR (CCl$_4$): 2919, 2816, 1703 and 1642 cm$^{-1}$.

MS (m/e): 198 (M⊕), 183, 166, 139 and 86.

PMR (CDCl$_3$): delta 1.7 (bt, methylene), 2.4 (m, methylenes), 3.7 (s, methyl), 4.0 (s, ethylene) and 7.0 (bm, olefinic H).

Analysis: Calc'd. for $C_{10}H_{14}O_4$: C, 60.17; H, 6.83. Found: C, 60.53; H, 7.11.

Repetition of this procedure but using an equivalent amount of diethylsulfate in place of dimethylsulfate affords the corresponding ethyl ester.

EXAMPLE 8

1,4-Dioxa-7-carbomethoxy-8-(2-oxopropyl)spiro[4,5]-decane

To a $-78°$ C. solution of 74 ml. (0.575 mole) of acetone dimethylhydrazone in 1.9 l. of tetrahydrofuran is added dropwise 288 ml. (0.575 mole) of butyllithium (2M in hexane). To the resultant cloudy solution is added dropwise a solution of 54.8 g. (0.288 mole) of cuprous iodide and 167 ml. (1.15 mole) of diisopropyl sulfide in 500 ml. of tetrahydrofuran. The resultant suspension is warmed to $-23°$ C. for 20 minutes, $0°$ C. for 5 minutes and the resultant solution cooled to $-78°$ C. To the above prepared cuprate solution is added dropwise 44.6 g. (0.225 mole) of 1,4-dioxa-7-carbomethoxyspiro[4.5]dec-7-ene. The resultant mixture is stirred 15 minutes at $-78°$ C. and then added to 4 l. of saturated ammonium chloride solution (pH adjusted to 8 with ammonium hydroxide). The reaction quench is extracted with 1 l. of ether and the extract washed with four 2 l. and one 1 l. portion of pH 8 saturated ammonium chloride. The organic extract is dried over magnesium sulfate and evaporated to yield 67 g. of intermediate hydrazone of the title compound. To the 67 g. of crude intermediate dissolved in 3 l. tetrahydrofuran and 625 ml. of pH 7 buffer is added a solution of 45.2 g. (0.339 mole) of cupric chloride in 1 l. of water. The hydrolysis mixture is stirred at $25°$ C. for 22 hours and then added to pH 8 saturated ammonium chloride solution and ether. The ether extract is washed with pH 8 saturated ammonium chloride until colorless, dried over magnesium sulfate and evaporated to an oil.

The above procedure is repeated on a scale of 42.5 g. (0.214 mole) of 1,4-dioxa-7-carbomethoxyspiro[4.5]dec-7-ene. The combined crude product from each preparation (113 g.) is purified via column chromatography on 3 kg. of silica gel eluted with 75% ether-petroleum ether to give 80.3 g. (71.2%) of the title compound as an oil.

IR (CHCl$_3$): 1730 and 1715 cm$^{-1}$.

HRMS (m/e): No M$^{\oplus}$, 224.1071 ($C_{17}H_{17}O_4$), 198, 157, 139 and 99.

PMR (CDCl$_3$): delta 1.5–2.0 (m), 2.12 (s, methyl ketone), 2.2–3.0 (m), 3.62 (s, methyl ester) and 3.92 (s, ethylene).

EXAMPLE 9

1,4-Dioxa-7-carboxy-8-(2-oxopropyl)spiro[4.5]decane

To a solution of 80.2 g. (0.313 mole) of 1,4-dioxa-7-carbomethoxy-8-(2-oxopropyl)spiro[4.5]decane in 500 ml. methanol and 1.6 l. tetrahydrofuran is added a solution of 36.1 g. (0.90 mole) of sodium hydroxide in 300 ml. of 5:16 methanol:tetrahydrofuran. The reaction mixture is stirred 30 minutes and then diluted with 500 ml. water and saturated with sodium chloride. The reaction mixture is cooled to $0°$ C., 500 ml. of ether added and acidified to pH 5 with concentrated hydrochloric acid. The quenched reaction is extracted once with 2 l. ether, the pH lowered to 3.5 and extracted with 1.5 l. ether and the pH lowered to 2.0 and extracted with two 1.5 l. portions of ether. The combined extract is dried over magnesium sulfate and evaporated to yield 72.5 g. (96%) of the title compound as an oil.

IR (CHCl$_3$): 2836 (broad) and 1702 cm$^{-1}$.

HRMS (m/e): 242.1185 (M$^{\oplus}$, calc'd for $C_{17}H_{18}O_5$: 242.1149), 224, 185, 184, 139, 99 and 86.

PMR (CDCl$_3$): delta 1.4–2.0 (m), 2.12 (s, methyl ketone), 2.2–3.4 (m), 3.95 (s, ethylene) and 9.97 (bs, COOH).

EXAMPLE 10

Trans-4a,5,8,8a-tetrahydro-(1H,6H)-3-methyl-2-benzopyran-1,7-dione-7-Ethylene Ketal A mixture of 72.5 g. (0.299 mole) of 1,4-dioxa-7-carboxy-8-(2-oxopropyl)spiro[4.5]decane and 14.3 g. (0.174 mole) of sodium acetate in 690 ml. of acetic anhydride is heated at reflux for 12 hours and stirred at $25°$ C. for 5.5 hours. The reaction mixture is poured onto 585 g. ice and 440 g. of sodium acetate, diluted with 200 ml. ether and slowly neutralized with 454 g. of solid sodium bicarbonate. The organic extract is dried over magnesium sulfate and evaporated. The crude residue is vacuum distilled to yield an oil which is dissolved in 100 ml. ether and washed twice with 100 ml. saturated sodium bicarbonate, once with 100 ml. saturated sodium chloride, dried over magnesium sulfate and evaporated to yield 63.0 g. (94%) of the title compound as an oil.

IR (CCl$_4$): 1770, 1695 and 1667 cm$^{-1}$.

HRMS (m/e): 224.1055 (M$^{\oplus}$, calc'd. for $C_{12}H_{16}O_4$: 224.1044), 195, 180, 153, 126, 99 and 86.

PMR (CDCl$_3$): delta 1.2–2.0 (m), 1.93 (bs, vinyl methyl), 2.0–3.0 (m), 3.99 (s, ethylene) and 4.90 (bs, vinyl H).

EXAMPLE 11

Trans-4a,5,8,8a-tetrahydronaphthalen-2(1H),6(7H)-dione-6-Ethylene Ketal

To a $-78°$ C. solution of 50.4 g. (0.225 mole) of trans-4a,5,8,8a-tetrahydro-(1H,6H)-3-methyl-2-benzopyran-1,7-dione 7-ethylene ketal in 504 ml. toluene is slowly added 236 ml. (0.236 mole) of diisobutylaluminum hydride (1M in hexane). The reaction is allowed to stir 15 minutes at $-78°$ C. and then a small portion of methanol is slowly added to remove any excess diisobutylaluminum hydride. The quenched reaction is added to 3 l. ether and washed successively with three 800 ml. portions of 50% saturated sodium potassium tartrate and one 800 ml. portion of saturated sodium chloride. The combined tartrate washes are extracted with 1.6 l. dichloromethane and 1.6 l. ether followed by washing of the combined extracts with 800 ml. saturated sodium chloride. All organic extracts are combined, dried over magnesium sulfate and evaporated to give a quantitative yield of intermediate ketoaldehyde. To the above prepared crude ketoaldehyde dissolved in 890 ml. benzene is added 16.0 g. (0.225 mole) of pyrrolidine and 9.2 g. (0.153 mole) of acetic acid. The reaction is stirred 4 hours at $25°$ C. and then diluted with 2 l. ether and washed with 600 ml. water, 600 ml. saturated sodium chloride, dried over magnesium sulfate and evaporated to an oil. This crude oil is purified via column chromatography on 1 kg. of silica gel eluted with 10% hexane-ether to give 10.6 g. (23%) of the title compound as an oil.

IR (CHCl$_3$): 1677 and 1615 cm$^{-1}$.

HRMS (m/e): 208.1100 (M$^{\oplus}$, calc'd. for $C_{12}H_{16}O_3$: 208.1095), 180, 152, 99 and 86.

PMR (CDCl$_3$): delta 1.2–3.4 (m), 4.00 (bs, ethylene), 5.98 (dd, J=10 and 3 Hz, vinyl H) and 6.71 (dd, J=10 and 2 Hz, vinyl H).

Following the procedure of Examples 7–10 and the above procedure, 1,5-dioxa-8-carboxy-2-methyl-spiro[5.5]undec-8-ene is converted to trans-4a,5,8,8a-tetrahydro-(1H,6H)-2-benzopyran-1,7-dione 1,3-butylene ketal.

J=8 and 2 Hz, ArH), 7.08 (d, J=8 Hz, ArH) and 7.37 (s, PhH).

The following compounds are prepared in like manner but using the appropriate 1-bromo-2-benzyloxy-4-(substituted)benzene in place of 1-bromo-2-benzyloxy-4-(1,1-dimethylheptyl)benzene.

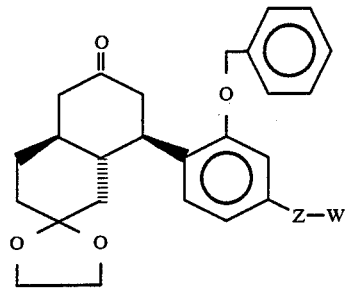

| Z | W | Z | W |
|---|---|---|---|
| C(CH$_3$)$_2$(CH$_2$)$_4$ | H | O(CH$_2$)$_7$ | H |
| (CH$_2$)$_8$ | H | OCH(CH$_3$)(CH$_2$)$_9$ | H |
| C(CH$_3$)$_2$(CH$_2$)$_6$ | H | OCH(CH$_3$)(CH$_2$)$_5$ | H |
| (CH$_2$)$_7$ | H | OC(CH$_3$)$_2$(CH$_2$)$_5$ | H |
| C(CH$_3$)$_2$(CH$_2$)$_8$ | H | OC(CH$_3$)$_2$(CH$_2$)$_7$ | H |
| CH(CH$_3$)CH(CH$_3$)(CH$_2$)$_5$ | H | O(CH$_2$)$_2$C(CH$_3$)$_2$(CH$_2$)$_2$ | H |
| (CH$_2$)$_{11}$ | H | O(CH$_2$)$_4$ | C$_6$H$_5$ |
| (CH$_2$)$_4$ | C$_6$H$_5$ | O(CH$_2$)$_6$ | C$_6$H$_5$ |
| CH(CH$_3$)(CH$_2$)$_5$ | C$_6$H$_5$ | OC(CH$_3$)$_2$(CH$_2$)$_3$ | C$_6$H$_5$ |
| CH(CH$_3$)(CH$_2$)$_3$ | C$_6$H$_5$ | OCH(CH$_3$)(CH$_2$)$_3$ | C$_6$H$_5$ |
| CH(CH$_3$)CH(CH$_3$)(CH$_2$)$_3$ | C$_6$H$_5$ | O(CH$_2$)$_4$ | 4F—C$_6$H$_4$ |
| (CH$_2$)$_7$ | C$_6$H$_5$ | OCH(CH$_3$)(CH$_2$) | 4F—C$_6$H$_4$ |
| CH(CH$_3$)(CH$_2$)$_3$ | 4-FC$_6$H$_4$ | OCH(CH$_2$)(CH$_2$)$_6$ | 4F—C$_6$H$_4$ |
| CH(C$_2$H$_5$)(CH$_2$)$_4$ | 4-FC$_6$H$_4$ | O(CH$_2$)$_8$ | 4Cl—C$_6$H$_4$ |
| CH(C$_2$H$_5$)(CH$_2$)$_2$ | 4-ClC$_6$H$_4$ | OCH(C$_2$H$_5$)(CH$_2$)$_3$ | 4Cl—C$_6$H$_4$ |
| CH(CH$_3$)(CH$_2$)$_3$ | 4-ClC$_6$H$_4$ | (CH$_2$)$_4$OCH$_2$ | C$_6$H$_5$ |
| (CH$_2$)$_4$ | 4-pyridyl | (CH$_2$)$_6$O | C$_6$H$_5$ |
| CH(CH$_3$)(CH$_2$)$_3$ | 4-pyridyl | CH(CH$_3$)(CH$_2$)$_2$O | C$_6$H$_5$ |
| CH(C$_2$H$_5$)CH$_2$ | 4-pyridyl | CH(CH$_3$)(CH$_2$)$_5$O | C$_6$H$_5$ |
| (CH$_2$)$_7$ | 4-pyridyl | (CH$_2$)$_6$O | 4-FC$_6$H$_4$ |
| CH(CH$_3$)CH(CH$_3$)CH$_2$ | 4-pyridyl | (CH$_2$)$_6$O | 4-ClC$_6$H$_4$ |
| CH(CH$_3$)CH(CH$_3$)CH$_2$ | 3-pyridyl | (CH$_2$)$_3$OCH(CH$_3$) | 2-pyridyl |
| CH(CH$_3$)(CH$_2$)$_3$ | 2-pyridyl | (CH$_2$)$_4$O | 4-pyridyl |
| (CH$_2$)$_3$O(CH$_2$)$_4$ | H | (CH$_2$)$_3$O(CH$_2$)$_4$ | 4-pyridyl |
| (CH$_2$)O(CH$_2$)$_7$ | H | CH$_2$CH(CH$_3$)O(CH$_2$)$_2$ | 4-pyridyl |
| C(CH$_3$)$_2$(CH$_2$)$_2$O(CH$_2$)$_2$ | H | O(CH$_2$)$_5$ | 3-pyridyl |
| (CH$_2$)$_7$O | H | O(CH$_2$)$_7$ | 2-pyridyl |
| (CH$_2$)$_{11}$O | H | OCH(CH$_3$)(CH$_2$)$_3$ | 2-pyridyl |
| CH(CH$_3$)(CH$_2$)$_6$O | H | CH$_2$O(CH$_2$)$_5$ | C$_6$H$_5$ |
| CH(CH$_3$)CH$_2$O(CH$_2$)$_4$ | C$_6$H$_5$ | CH(CH$_3$)CH$_2$OCH$_2$ | 4-ClC$_6$H$_4$ |
| (CH$_2$)$_3$OCH(CH$_3$) | C$_6$H$_5$ | CH$_2$O(CH$_2$)$_5$ | 4-FC$_6$H$_4$ |
| (CH$_2$)$_5$O | H | (CH$_2$)$_3$O | C$_6$H$_5$ |
| (CH$_2$)$_9$(CH$_2$)$_4$ | H | (CH$_2$)$_3$O(CH$_2$)$_5$ | C$_6$H$_5$ |

EXAMPLE 12

3,4-alpha,4a-beta,5,8,8a-alpha-Hexahydro-4-beta-[2-benzyloxy-4-(1,1-dimethylheptyl)phenyl]-naphthalen-2(1H),6(7H)-dione 6-Ethylene Ketal Using the procedure of Example 1, 23.3 g. (60 mmole) of 1-bromo-2-benzyloxy-4-(1,1-dimethylheptyl)benzene and 10.0 g. (48.1 mmole) of trans-4a,5,8,8a-tetrahydro-naphthalen-2(1H),6(7H)-dione 6-ethylene ketal are reacted together to give 9.94 g. (40%) of the title compound as an oil.

IR (CHCl$_3$): 1712, 1613 and 1575 cm$^{-1}$.

HRMS (m/e): 518.3390 (M$^\oplus$, calc'd. for C$_{34}$H$_{46}$O$_4$: 518.3392), 433, 273, 243, 153, 140 and 91.

PMR (CDCl$_3$): delta 0.82 (m, terminal methyl), 1.23 (s, gem dimethyl), 3.83 (bs, ethylene ketal), 5.05 (s, benzyl ether methylene), 6.84 (d, J=2 Hz, ArH), 6.84 (dd,

EXAMPLE 13

1,2-alpha,3,4-alpha,4a-beta,5,8,8a-alpha-Octahydro-4-beta-[2-benzyloxy-4-(1,1-dimethylheptyl)phenyl-2-beta-hydroxy-naphthalen-6(7H)-one 6-Ethylene Ketal and Its 2-alpha Isomer Using the procedure of Example 2 9.8 g. (18.9 mmole) of 3,4-alpha,4a-beta,5,8,8a-alpha-hexahydro-4-beta-[2-benzyloxy-4-(1,1-dimethylheptyl)phenyl]-naphthalen-2(1H),6(7H)-dione 6-ethylene ketal, the title product of Example 12, is reduced to 1.5 g. (15%) of the 6-alpha isomer of the title compound, 1.75 g. (18%) of mixture and 4.0 g. (41%) of the title compound.

Title Compound:

IR (CHCl$_3$): 5597, 3448, 1618 and 1582 cm$^{-1}$.

HRMS (m/e): 520.3580 (M$^\oplus$, calc'd. for C$_{34}$H$_{48}$O$_4$: 520.3548), 435, 244, 243, 154, 153, 140 and 91.

PMR (CDCl₃): delta 0.81 (m, terminal methyl), 1.22 (s, gem dimethyl), 3.2 (m, benzylic methine), 3.8 (m, carbinol methine and ethylene ketal), 5.02 (s, benzylic methylene), 9.0 (m, ArH), 7.07 (d, J=8 Hz, ArH) and 7.35 (s, PhH).

2-alpha Isomer of the Title Compound:

IR (CHCl₃): 3448, 1613 and 1578 cm⁻¹.

HRMS (m/e): 520.3496 (M⊕, calc'd. for C₃₄H₄₈O₄: 520.3548), 435, 323, 244, 243 and 91.

PMR (CDCl₃): 0.82 (m, terminal methyl), 1.22 (s, gem dimethyl), 3.4 (m, benzylic methine), 3.80 (bs, ethylene ketal), 4.12 (m, carbinol methine), 5.02 (s, benzylic methylene), 6.88 (s, ArH), 7.07 (d, J=8 Hz, ArH) and 7.38 (m, PhH).

Reduction of the remaining compounds of Example 12 in like manner affords their corresponding isomeric 2-hydroxynaphthalen-6(7H)-ones of the formula

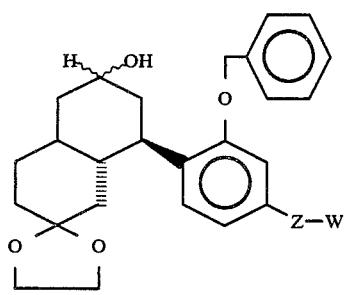

wherein Z and W are as defined in Example 12.

EXAMPLE 14

1,2-alpha,3,4-alpha,4a-beta,5,8,8a-alpha-Octahydro-4-beta-[2-benzyloxy-4-(1,1-dimethylheptyl)-phenyl]-2-beta-hydroxy-naphthalen-6(7)-one A mixture of 2.0 g. (3.85 mmole) of 1,2-alpha,3,4-alpha,4a-beta,5,8,8a-alpha-octahydro-4-beta-[2-benzyloxy-4-(1,1-dimethylheptyl)phenyl]-2-beta-hydroxy-naphthalen-6(7H)-one 6-ethylene ketal, the title compound of Example 13, in 50 ml. tetrahydrofuran and 25 ml. 1N hydrochloric acid is heated at 70° C. for 4 hours. The reaction is cooled and added to 250 ml. saturated sodium chloride-300 ml. ether. The ether extract is washed twice with 250 ml. portions of saturated sodium bicarbonate, dried over magnesium sulfate and evaporated to yield 1.9 g. (100%) of the title compound as an oil.

IR (CHCl₃): 3425, 1709, 1608 and 1575 cm⁻¹.

HRMS (m/e): 476.3278 (M⊕, calc'd. for C₃₂H₄₄O₃: 476.3285), 371, 259, 233, 200, 147 and 91.

PMR (CDCl₃): delta 0.84 (m, terminal methyl), 1.22 (s, gem dimethyl), 3.2 (m, benzylic methine), 3.85 (m, carbinol methine), 5.05 (s, benzylic methylene), 6.9 (m, ArH), 7.03 (d, J=8 Hz, ArH) and 7.38 (s, PhH).

Acid treatment of the remaining compounds of Example 13 affords the corresponding 2-hydroxynaphthalen-6(7H)-ones.

EXAMPLE 15

1,2-alpha,3,4-alpha,4a-beta,5,8,8a-alpha-Octahydro-4-beta-[4-(1,1-dimethylheptyl)-2-hydroxyphenyl]-2-beta-hydroxy-naphthalen-6(7H)-one Following the procedure of Example 3 330 mg. (0.692 mmole) of 1,2-alpha,3,4-alpha,4a-beta,5,8,8a-alpha-octahydro-4-beta-[2-benzyloxy-4-(1,1-dimethyl-heptyl)phenyl]-2-beta-hydroxy-naphthalen-6(7H)-one is reduced to give 218 mg. of the title compound.

MP: 160°–161° C. (acetonitrile).

IR (CHCl₃): 3571, 3333, 1706, 1621 and 1582 cm⁻¹.

HRMS (m/e): 386.2844 (M⊕, calc'd. for C₂₅H₃₈O₃: 386.2817), 368, 301, 283 and 110.

PMR (100 MHz, CDCl₃): delta 0.82 (bt, J=6 Hz, terminal methyl), 1.24 (s, gem dimethyl), 3.08 (m, benzylic methine), 3.32 (bd, J=4 Hz, OH), 3.82 (m, carbinol methine), 6.7 (m, ArH), 6.96 (d, J=8 Hz, ArH) and 8.1 (bs, OH).

Following the procedure of Example 14 and the above procedure the tabulated compounds of Example 13 are converted to compounds having the formula shown below wherein Z and W are as defined in Example 13:

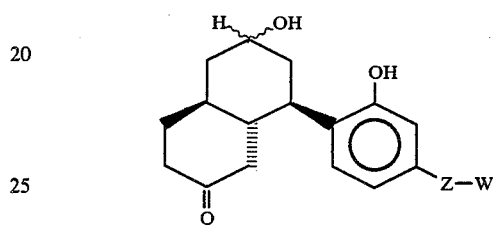

EXAMPLE 16

1,2-alpha,3,4-alpha,4a-beta,5,6-beta,7,8,8a-alpha-Decahydro-4-beta-[2-benzyloxy-4-(1,1-dimethylheptyl)-phenyl]-naphthalen-2-beta,6-alpha-diol Following the procedure of Example 2, reduction of 500 mg. (1.05 mmole) of 1,2-alpha,3,4-alpha,4a-beta,5,8,8a-alpha-octahydro-4-beta-[2-benzyloxy-4-(1,1-dimethylheptyl)phenyl]-2-beta-hydroxy-naphthalen-6(7H)-one, the title product of Example 14, gives a quantitative yield of the title compound as an oil.

PMR (CDCl₃): delta 0.84 (m, terminal methyl), 1.25 (s, gem dimethyl), ~3.0 (m, benzylic methine), 3.8 (bm, carbinol methine), 5.02 (s, benzylic methylene), 6.95 (m, ArH), 7.10 (d, J=8 Hz, ArH) and 7.40 (s, PhH).

EXAMPLE 17

1,2-alpha,3,4-alpha,4a-beta,5,6-alpha,7,8,8a-alpha-Decahydro-4-beta-[2-benzyloxy-4-(1,1-dimethylheptyl)-phenyl]-naphthalen-2-beta,6-beta-diol To a 25° C. solution of 400 mg. (0.84 mmole) of the title product of Example 14, 1,2-alpha,3,4-alpha,4a-beta,5,8,8a-alpha-octahydro-4-beta-[2-benzyloxy-4-(1,1-dimethylheptyl)phenyl]-2-beta-hydroxy-naphthalen-6(7H)-one in 2 ml. of tetrahydrofuran is added 5.04 ml. (2.52 mmole) of potassium tri-sec-butylborohydride (0.5M) in tetrahydrofuran). The reaction is stirred 30 minutes, cooled to 0° C. and then oxidized with 10 ml. tetrahydrofuran, 30 ml. 1N sodium hydroxide and 6 ml. 30% hydrogen peroxide. After 30 minutes the reaction is added to 250 ml. saturated sodium chloride and 300 ml. ether. The ether extract is washed once with 250 ml. saturated sodium chloride, dried over magnesium sulfate and evaporated to an oil. This crude oil is purified via column chromatography on 100 g. of silica gel eluted in 10 ml. fractions with 1 l. of 50% ether-hexane and then 100% ether to yield 283 mg. (71%) of the title compound as an oil.

$R_f$=0.23 (0.25 mm silica gel; ether).

Reduction of the remaining compounds of Example 14 according to the above procedure affords the corresponding 2-beta,6-beta-naphthalenediols.

EXAMPLE 18

1,2-alpha,3,4-alpha,4a-beta,5,6-beta,7,8,8a-alpha-Decahydro-4-beta-[4-(1,1-dimethylheptyl)-2-hydroxyphenyl]-naphthalen-2-beta,6-alpha-diol Following the procedure of Example 3, catalytic reduction of 502 mg. (1.05 mmole) of crude 1,2-alpha,3,4-alpha,4a-beta,5,6-beta,7,8,8a-alpha-decahydro-4-beta-[2-benzyloxy-4-(1,1-dimethylheptyl)phenyl]-naphthalen-2-beta,6-alpha-diol gives 300 mg. (74%) of the title compound as a foam.

PMR (100 MHz, CDCl$_3$): delta 0.83 (m, terminal methyl), 2.84 (m, benzylic methine), 3.47 and 3.87 (m, carbinol methines), 6.80 (m, ArH) and 6.99 (d, J=8 Hz, ArH).

HRMS (m/e): 388.2781 (M$^\oplus$, calc'd. for $C_{25}H_{40}O_3$: 388.2973), 370, 352, 303, 285 and 267.

EXAMPLE 19

1,2-alpha,3,4-alpha,4a-beta,5,6-alpha,7,8,8a-alpha-Decahydro-4-beta-[4-(1,1-dimethylheptyl)-2-hydroxyphenyl]-naphthalen-2-beta,6-beta-diol Following the procedure of Example 3, 283 mg. (0.592 mmole) 1,2-alpha,3,4-alpha,4a-beta,5,6-alpha,7,8,8a-alpha-decahydro-4-beta-[2-benzyloxy-4-(1,1-dimethylheptyl)-phenyl]-naphthalen-2-beta,6-beta-diol is reduced to provide 145 mg. (63%) of the title compound.

MP: 91°-2° C. (diisopropyl ether).

PMR (100 MHz, CDCl$_3$): delta 0.85 (m, terminal methyl), 1.20 (s, gem dimethyl), 280 (m, benzylic methine), 3.80 (bm, carbinol methine), 4.03 (m, carbinol methine), 6.85 (m, ArH) and 7.12 (d, J=8 Hz, ArH).

HRMS (m/e): 388.2985 (M$^\oplus$, calc'd. for $C_{25}H_{40}O_3$: 388.2973), 370, 352, 303, 285 and 267.

In like manner, the compounds of Examples 16 and 17 are reduced to provide compounds of the formula below wherein Z and W are as defined in said Examples.

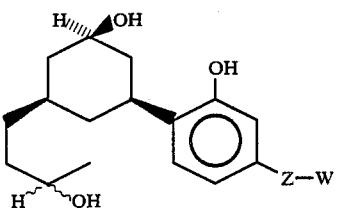

EXAMPLE 20

1,2-alpha,3,4-alpha,4a-beta,5,8,8a-alpha-Octahydro-4-beta-[2-benzyloxy-4-(1,1-dimethylheptyl)-phenyl]-6(7H)-methylene-naphthalen-2-beta-ol To a 15° C. mixture of triphenylphosphorous methylide [from 2.25 g. (6.30 mmoles) of methyltriphenylphosphonium bromide and 151 mg. (6.30 mmole) of sodium hydride] in 7 ml. of dimethyl sulfoxide is added a solution of 1.0 g. (2.10 mmole) of 1,2-alpha,3,4-alpha,-4a-beta,5,8,8a-alpha-octahydro-4-beta-[2-benzyloxy-4-(1,1-dimethylheptyl)phenyl]-2-beta-hydroxy-naphthalen-6(7H)-one, the title compound of Example 14, in 3 ml. of dimethyl sulfoxide and 5 ml. of tetrahydrofuran. The reaction mixture is stirred 20 minutes and then added to 250 ml. of water, 200 ml. ether and 100 ml. pentane. The organic extract is washed with two 125 ml. portions of water, dried over magnesium sulfate and evaporated. Triphenylphosphine oxide is removed from the crude product by crystallization in ether-pentane. The title compound is obtained upon evaporation of the filtrate in quantitative yield as an oil.

R$_f$=0.22 (0.25 mm silica gel; 50% ether-hexane).

PMR (CDCl$_3$): delta 0.82 (m, terminal methyl), 1.23 (s, gem dimethyl), 3.02 (m, benzylic methine), 3.7 (m, carbinol methine), 4.43 (m, vinyl methylene), 5.02 (s, benzylic methylene), 6.85 (m, ArH), 7.04 (d, J=8 Hz, ArH) and 7.33 (s, Ph).

By means of the above procedure the remaining compounds of Example 14 are converted to their 6-methylene derivatives.

EXAMPLE 21

1,2-alpha,3,4-alpha,4a-beta,5,6-beta,7,8,8a-alpha-Decahydro-4-beta-[2-benzyloxy-4-(1,1-dimethylheptyl)phenyl]-6-alpha-hydroxymethyl-naphthalen-2-beta-ol and Its 6-beta-Isomer To a 0° C. solution of 925 mg. (2.10 mmole) 1,2-alpha,3,4-alpha,4a-beta,5,8,8a-alpha-octahydro-4-beta-[2-benzyloxy-4-(1,1-dimethylheptyl)phenyl]-6(7H)-methylene-naphthalen-2-beta-ol, the title compound of Example 20, in 10 ml. of tetrahydrofuran is added 4.2 ml. (4.20 mmole) of borane tetrahydrofuran complex (1M in tetrahydrofuran). The reaction is stirred 45 minutes and then oxidized by the addition of 6.3 ml. (12.6 mmole) of 2N sodium hydroxide and 1.08 ml. (12.6 mmole) of 30% hydrogen peroxide. After stirring 30 minutes the reaction mixture is added to 500 ml. saturated sodium chloride and 300 ml. ether. The organic extract is washed once with 250 ml. of saturated sodium chloride, dried over magnesium sulfate and evaporated to an oil. Purification of the crude product via column chromatography on 100 g. of silica gel eluted with 2:1 ether:hexane gives in order of elution 275 mg. (27%) of the title compound and 670 mg. (65%) of the 6-beta-isomer of the title compound.

Title Compound:

HRMS (m/e): 492.3605 (M$^\oplus$, calc'd. for $C_{33}H_{48}O_3$: 492.3597), 407, 389, 384, 299 and 91. 6-beta-Isomer of the Title Compound:

HRMS (m/e): 492.3555 (M$^\oplus$, calc'd. for $C_{33}H_{48}O_3$: 492.3597), 407, 389, 384, 299 and 91.

EXAMPLE 22

1,2-alpha,3,4-alpha,4a-beta,5,6-beta,7,8,8a-Decahydro-4-beta-[4-(1,1-dimethylheptyl-2-hydroxyphenyl]-6-alpha-hydroxymethyl-naphthalen-2-beta-ol Catalytic reduction of 270 mg. (0.548 mmole) of 1,2-alpha,3,4-alpha,4a-beta,5,6-beta,7,8,8a-alpha-decahydro-4-beta-[2-benzyloxy-4-(1,1-dimethylheptyl)phenyl]-6-alpha-hydroxymethyl-naphthalen-2-beta-ol according to the procedure of Example 3 gives 178 mg. (81%) of the title compound as a foam.

HRMS (m/e): 402.3109 (M$^\oplus$, calc'd. for $C_{26}H_{42}O_3$: 402.3129), 384, 317, 299 and 147.

PMR (270 MHz, CDCl$_3$): delta 0.94 (t, J=7 Hz, terminal methyl), 1.39 (s, gem dimethyl), 3.11 (m, benzylic methine), 3.70 (m, hydroxymethylene), 4.19 (m, carbinol methine), 6.27 (s, OH), 7.43 (bs, ArH), 7.59 (bd, J=8 Hz, ArH) and 7.80 (d, J=8 Hz, ArH).

EXAMPLE 23

1,2-alpha,3,4-alpha,4a-beta,5,6-alpha,7,8,8a-alpha-Decahydro-4-beta-[4-(1,1-dimethylheptyl)-2-hydroxyphenyl]-6-beta-hydroxymethyl-naphthalen-2-beta-ol Reduction of 660 mg. (1.34 mmole) of 1,2-alpha,3,4-alpha,4-a-beta,5,6-alpha,7,8,8a-alpha-decahydro-4-beta-[2-benzyloxy-4-(1,1-dimethylheptyl)phenyl]-6-beta-hydroxymethyl-naphthalen-2-beta-ol according to the method of Example 3 gives 421 mg. (78%) of the title compound as an oil.

HRMS (m/e): 402.3109 (M⊕, calc'd. for $C_{26}H_{42}O_3$: 402.3129), 384, 317, 299, 161 and 147.

PMR (270 MHz, CDCl$_3$): delta 0.96 (t, J=7 Hz, terminal methyl), 1.35 (s, gem dimethyl), 3.07 (m, benzylic methine), 4.00 (m, hydroxymethylene), 4.22 (m, carbinol methine), 6.20 (s, OH), 7.43 (bs, ArH), 7.59 (bd, J=8 Hz, ArH) and 7.76 (d, J=8 Hz, ArH).

By means of the procedure of Example 21 and of the above procedure, the 6-methylene derivatives of Example 20 are converted to corresponding 6-hydroxymethyl derivatives having the formula wherein Z and W are as defined in Example 20.

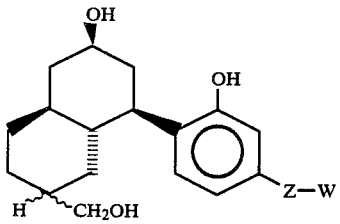

EXAMPLE 24

1,2-alpha,3,4-alpha,4a-beta,5,6-alpha,7,8,8a-alpha-Decahydro-4-beta[2-Benzyloxy-4-(1,1-dimethylheptyl)-phenyl]-2-beta-(d-Mandeloyloxy)-6-beta-(d-Mandeloyloxy)methyl Naphthalene A mixture of 940 mg. (1.91 mmole) of 1,2-alpha,3,4-alpha,4a-beta,5,6-alpha,7,8,8a-alpha-decahydro-4-beta-[2-benzyloxy-4-(1,1-dimethylheptyl)phenyl]-6-beta-hydroxymethylnaphthalene-2-beta-ol, 912 mg. (6.00 mmole) of d-mandelic acid and 38 mg. (0.2 mmole) of p-toluenesulfonic acid monohydrate in 15 ml. of benzene is heated at reflux for 11 hours. Water is removed via a soxhlet extractor filled with 3A molecular sieves. The reaction is cooled and diluted in 250 ml. ether—250 ml. saturated sodium bicarbonate. The organic extract is dried over magnesium sulfate and evaporated to yield an oil. The crude oil is purified via column chromatography on 200 g. of silica gel eluted with 50% ether-hexane to yield, in order of elution, 481 mg. (crystallized from diisopropyl ether) (33%) of diastereomer A and 352 mg. (24%) of diastereomer B as an oil.

Diastereomer A of Title Compound:
MP: 148°-9° C. (from diisopropyl ether).
[alpha]$_D^{20°}$ = +17.84° (c=0.419, 20:1 CH$_3$OH:CHCl$_3$).

PMR (CDCl$_3$, 100 MHz): delta 0.82 (m, terminal methyl), 1.24 (s, gem dimethyl), 2.95 (m, benzylic methine), 3.42 and 3.44 (d, J=6 Hz, OH), 4.08 (m, methylene), 4.85 (m, methine), 4.94 and 5.10 (d, J=6 Hz, methines), 5.08 (s, benzylic methylene), 6.92 (m, ArH), 7.27 (s, PhH) and 7.40 (m, PhH).

Analysis: Calc'd. for $C_{49}H_{60}O_7$: C, 77.33; H, 7.95. Found: C, 77.40; H, 8.14.

Diastereomer B of Title Compound:
[alpha]$_D^{20°}$ = +51.34° (c=1.073, 20:1 CH$_3$OH:CHCl$_3$).

PMR (CDCl$_3$, 100 MHz): 0.80 (m, terminal methyl), 1.20 (s, gem dimethyl), 2.90 (m, benzylic methine), 3.28 and 3.43 (d, J=6 Hz, OH), 4.07 (m, methylene), 4.83 (m, methine), 4.99 (s, benzylic methylene), 5.05 and 5.09 (d, J=6 Hz, methines), 6.84 (m, ArH), 7.28 (s, PhH) and 7.31 (m, PhH).

EXAMPLE 25

1,2-alpha,3,4-alpha,4a-beta,5,6-alpha,7,8,8a-alpha-Decahydro-4-beta-[2-Benzyloxy-4-(1,1-dimethylheptyl)phenyl]6-beta-Hydroxymethylnaphthalen-2-beta-ol (Enantiomer A)

A mixture of 590 mg. (0.776 mmole) of 1,2-alpha,3,4-alpha,4a-beta,5,6-alpha,7,8,8a-alpha-decahydro-4-beta-[2-benzyloxy-4-(1,1-dimethylheptyl)phenyl]-2-beta-(d-mandeloyloxy)-6-beta-(d-mandeloyloxy)methylnaphthalene, diastereomer A, and 429 mg. (3.11 mmole) of potassium carbonate in 7 ml. methanol—2 ml. tetrahydrofuran—1 ml. water is stirred 20 hours at 25° C. The reaction is added to 250 ml. ether—250 ml. saturated sodium bicarbonate. The organic extract is dried over magnesium sulfate and evaporated to give a quantitative yield of the title compound.

HRMS (m/e): 492.3614 (M+, calc'd. for $C_{33}H_{45}O_3$: 492.2277), 407, 299 and 91.

In like manner, 596 mg. (0.784 mmole) of the B diastereomer of the above reactant affords a quantitative yield of the B enantiomer of the title compound as an oil.

EXAMPLE 26

1,2-alpha,3,4-alpha,4a-beta,5,6-alpha,7,8,8a-alpha-Decahydro-4-beta-[2-Hydroxy-4-(1,1-dimethylheptyl)-phenyl]-6-beta-hydroxymethyl-2-beta-naphthalenol, Enantiomer A Using the procedure of Example 3, 2.54 g. (5.17 mmole) of 1,2-alpha-3,4-alpha,4a-beta,5,6-alpha,7,8,8a-alpha-decahydro-4-beta-[2-benzyloxy-4-(1,1-dimethylheptyl)phenyl]-6-beta-hydroxymethyl-2-beta-naphthalenol, diastereomer A, gives 2.0 g. (97%) of the title compound.

MP: 115°–116° C. (from ethyl acetate-hexane).
Analysis: Calc'd. for $C_{26}H_{42}O_3$: C, 77.56; H, 10.52. Found: C, 77.66; H, 10.19.
[alpha]$_D^{20°}$ C. = −28.68° (c=1.55, CH$_3$OH).

PMR (CDCl$_3$, 100 MHz): delta 0.81 (m, terminal methyl), 1.19 (s, gem dimethyl), 2.70 (m, benzylic methine), 3.36–3.98 (m), 5.58 (bs, OH) and 6.56–7.06 (m, ArH).

HRMS (m/e): 402.3167 (M⊕, calc'd. for $C_{26}H_{42}O_3$: 402.3123) 384, 317, 249, 161 and 147.

Similarly, 356 mg. (0.784 mmole) of enantiomer B affords 306 mg. (97% yield) of the B enantiomer of the title compound as a glass.

[alpha]$_D^{20°}$ C. = +27.98° (c=1.047, CH$_3$OH).

PMR (CDCl$_3$, 100 MHz): delta 0.81 (m, terminal methyl), 1.19 (s, gem dimethyl), 2.70 (m, benzylic methine), 3.36–3.98 (m), 5.58 (bs, OH) and 6.56–7.06 (m, ArH).

HRMS (m/e): 402.3154 (M⊕, calc'd. for $C_{26}H_{42}O_3$: 402.3123) 384, 317, 300 and 299.

EXAMPLE 27

1,2-alpha,3,4-alpha,4a-beta,5,6,7,8,8a-alpha-Decahydro-4-beta-[4-(1,1-dimethylhepthyl)-2-hydroxyphenyl]-6-methylnaphthalen-2-beta-ol Catalytic hydrogenation of 1.0 g. (2.11 mmole) of 1,2-alpha,3,4-alpha,4a-beta,5,8,8a-alpha-octahydro-4-beta-[2-benzyloxy-4-(1,1-dimethylheptyl)phenyl]-6(7H)-methylenenaphthalen-2-ol, the title compound of Example 20, according to the procedure of Example 3 affords the title compound as a mixture of the isomeric 6-methyl derivatives.

The remaining 6-methylene compounds of Example 20 are reduced in like manner to the corresponding 6-methyl derivatives.

EXAMPLE 28

General Hydrochloride Salt Formation

Excess hydrogen chloride is passed into a methanol solution of the appropriate compound of formula I having a basic group and ether added to the resulting mixture to insure maximum precipitation of the salt.

In this manner, compounds of formula I described herein which have a basic group are converted to their hydrochloride, hydrobromide, sulfate, nitrate, phosphate, acetate, butyrate, citrate, malonate, maleate, fumarate, malate, glycolate, gluconate, lactate, salicylate, sulfosalicylate, succinate, pamoate, tartrate and embonate salts.

EXAMPLE 29

1,2-alpha-3,4-alpha,4a-beta,5,6,7,8,8a-alpha-Decahydro-2-beta-Acetoxy-4-beta-[2 acetoxy-4-(1,1-dimethylheptyl)phenyl]-naphthalene A solution of 2.0 g. of 1,2,3,4-alpha,4a-beta,5,6,7,8,8a-alpha-decahydro-[4-(1,1-dimethylheptyl)-2-hydroxy)-phenyl]-naphthalen-2-beta-ol in 20 ml. of pyridine is treated at 10° C. with 20 ml. acetic anhydride and the mixture stirred for 18 hours under nitrogen. It is then poured onto ice/water and acidified with dilute hydrochloric acid. The acidified mixture is extracted with ethyl acetate (2×100 ml.), the extracts combined, washed with brine and dried (MgSO$_4$). Evaporation under reduced pressure gives the title product as an oil.

Similarly, substitution of anhydrides of propionic, butyric and valeric acid for acetic anhydride affords the corresponding ester derivatives.

Reduction of the 2-oxo group by means of sodium borohydride according to the procedure of Example 2 affords the corresponding 2-hydroxy derivatives, both isomers being formed.

EXAMPLE 30

3,4-alpha,4a-beta,5,6,7,8,8a-alpha-Octahydro-4-beta-[2-acetoxy-4-(1,1-dimethylheptyl)phenyl]-naphthalen-2(1H)-one Repetition of the procedure of Example 29 but using 10 ml. each of pyridine and acetic anhydride and 3,4-alpha,4a-beta,5,6,7,8,8a-alpha-octahydro-4-beta-[4-(1,1-dimethylheptyl)-2-hydroxyphenyl]naphthalen-2(1H)-one (2.0 g.) as reactant affords the title compound as an oil.

Replacement of acetic anhydride by propionic, butyric or valeric acid anhydrides affords the corresponding alkanoyl derivatives.

Sodium borohydride reduction of the 2-oxo group according to the procedure of Example 2 affords an isomeric mixture of the corresponding 2-hydroxy derivatives.

EXAMPLE 31

1,2-alpha,3,4-alpha,4a-beta,5,6-alpha,7,8,8a-alpha-Decahydro-2-beta-acetoxy-4-beta-[2-acetoxy-4-(1,1-dimethylheptyl)-phenyl]-6-beta-acetoxymethyl-naphthalene Following the procedure of Example 29, 2.0 g. of 1,2-alpha,3,4-alpha,4a-beta,5,6-alpha,7,8,8a-alpha-decahydro-4-beta-[4-(1,1-dimethylheptyl)-2-hydroxyphenyl]-6-beta-hydroxymethylnaphthalen-2-beta-ol is acetylated using 30 ml. each of acetic anhydride and 30 ml. of pyridine to give the title product.

Substitution of acetic anhydride by valeric acid anhydride provides the corresponding trivaleryl derivative.

EXAMPLE 32

1,2-alpha,3,4-alpha,4a-beta,5,6-alpha,7,8,8a-alpha-Decahydro-4-beta-[4-(1,1-dimethylheptyl)-2-hydroxyphenyl]-6-beta-(4-morpholinobutyryloxymethyl)naphthalen-2-beta-ol hydrochloride Dicyclohexylcarbodiimide (1.0 mmole) and 4-N-piperidylbutyric acid hydrochloride (1.0 mmole) are added to a solution of 1,2-alpha,3,4-alpha,4a-beta,5,6-alpha,7,8,8a-alpha-decahydro-4-beta-[4-(1,1-dimethylheptyl)-2-hydroxyphenyl]-6-beta-hydroxymethylnaphthalen-2-beta-ol (1.0 mmole) in methylene chloride at room temperature. The mixture is stirred for 18 hours, then cooled to 0° C. and filtered. Evaporation gives the title product. Also produced are the corresponding ester wherein acylation has occurred at the phenolic hydroxy group and the diester wherein the phenolic hydroxy group and the 6-hydroxymethyl group are esterified.

PREPARATION A

Methyl 3-benzyloxybenzoate

A mixture of 1564 g. (10.2 mole) of methyl 3-hydroxybenzoate, 1407.6 g. (10.2 mole) potassium carbonate and 1285.2 g. (10.2 mole) benzyl chloride in 5 l. of acetone is heated at reflux for 22 hours. The reaction mixture is then cooled, filtered and the filtrate evaporated. The residue is crystallized in a small volume of pentane to give a quantitative yield of the title compound.

MP: 74°–77° C. (Pentane).

IR (CHCl$_3$): 1724, 1587, 1486, and 1449 cm$^{-1}$.

MS (m/e): 242 (M+), 211 and 91.

PMR (CDCl$_3$): delta 3.95 (s, methyl), 5.10 (s, methylene), 7.2 (m, ArH), 7.35 (m, PhH) and 7.65 (m, ArH).

Analysis: Calc'd. for C$_{15}$H$_{14}$O$_3$: C, 74.38; H, 5.78. Found: C, 74.58; H, 6.09.

PREPARATION B

3-Benzyloxybenzene-2-propanol

To a 0° solution of 2.2 mole of methyl magnesium iodide in 1.5 l. ether is added a solution of 200 g. (1.06 mole) of methyl 3-benzyloxybenzoate in 500 ml. ether and 500 ml. tetrahydrofuran. The reaction mixture is stirred for 3 hours and then added to 1.5 l. ice cold saturated ammonium chloride and 2 l. ether. The organic extract is dried over magnesium sulfate and evaporated to an oil. Crystallization of the crude oil in petroleum ether gives 186 g. (93%) of the title compound.

MP: 45°–48° C. (Petroleum ether).

IR (CHCl$_3$): 3509, 3333, 1587, 1570, 1475 and 1443 cm$^{-1}$.

MS (m/e): 242 (M+), 225 and 91.

PMR (CDCl$_3$): delta 1.85 (s, gem dimethyl), 2.05 (s, OH), 5.1 (s, benzylic methylene), 7.2 (m, ArH) and 7.45 (bs, PhH).

PREPARATION C 2-(3-Benzyloxyphenyl)-2-chloropropane

A mixture of 200 g. (0.826 mole) of 3-benzyloxybenzene-2-propanol in 50 ml. of hexane and 1 l. of concentrated hydrochloric acid is shaken for 15 minutes in a 2 l. separatory funnel. The organic layer is removed and washed with saturated sodium bicarbonate. The neutralized organic extract is dried over magnesium sulfate and evaporated to give a quantitative yield of the title compound as an oil.

PMR (CDCl$_3$): delta 1.98 (s, gem dimethyl), 5.03 (s, benzylic methylene), 6.8-7.7 (m, ArH) and 7.38 (bs, PhH).

2-(3-Benzyloxyphenyl)-2-bromopropane

In a similar manner 5.0 g. (20.6 mmole) of 3-benzyloxybenzene 2-propanol and 200 ml. of 35% hydrobromic acid gives a quantitative yield of the title compound as an oil.

PMR (CDCl$_3$): delta 2.14 (s, gem dimethyl), 5.00 (s, benzylic methylene), 6.6-7.5 (m, ArH) and 7.33 (bs, PhH).

PREPARATION D

1-Benzyloxy-3-(1,1-dimethylheptyl)benzene

To a 0° C. mixture of 10.1 mmole of n-hexyl magnesium bromide in 5 ml. of hexane is added dropwise a solution of 2.0 g. (7.69 mmole) of 2-(3-benzyloxyphenyl)-2-chloropropane in 14 ml. of hexane. The reaction mixture is stirred 5 minutes longer and then added to 500 ml. of saturated ammonium chloride and 300 ml. ether. The organic extract is dried over magnesium sulfate and evaporated to an oil. The oil is purified via column chromatography on 150 g. of silica gel eluted with hexane to yield 841 mg. (35) of the title compound as an oil.

IR (CHCl$_3$): 1600, 1575, 1481, 1471 and 1447 cm$^{-1}$.

MS (m/e): 310 (M+), 225 and 91.

PMR (CDCl$_3$): delta 0.84 (terminal methyl), 1.28 (s, gem dimethyl), 5.04 (s, benzylic methylene), 6.7-7.6 (m, ArH) and 7.42 (bs, PhH).

PREPARATION E

2-Benzyloxy-1-bromo-4-(1,1-dimethylheptyl)benzene

To a −78° C. solution of 42.6 g. (0.134 mole) of 1-benzyloxy-3-(1,1-dimethylheptyl)benzene and 12.2 g. (0.200 mole) of t-butylamine in 300 ml. of dichloromethane is added a solution of 27.2 g. (0.151 mole), bromine in 100 ml. of dichloromethane. The reaction mixture is then allowed to warm to 25° C. and added to 500 ml. saturated sodium sulfite and 500 ml. ether. The organic extract is washed with two 500 ml. portions of saturated sodium bicarbonate, dried over magnesium sulfate and evaporated to an oil. The crude product is purified via column chromatography on 500 g. of silica gel eluted with 10% ether-hexane to give 41.9 g. (80%) of the title compound as an oil.

IR (CHCl$_3$): 1587, 1570 and 1481 cm$^{-1}$.

MS (m/e): 390, 338 (M+), 309, 299 and 91.

PMR (CDCl$_3$): delta 0.80 (m, terminal methyl), 1.20 (s, gem dimethyl), 5.05 (s, benzylic methylene), 6.8 (m, ArH) and 7.35 (m, ArH and PhH).

PREPARATION F

Trans-4a,5,8,8a-Tetrahydronaphthalen-2(1H),6(7H)-dione 6-Ethylene Ketal (a)

3-alpha-Phenylthio-decahydro-2,6-naphthalenedione 6-monoethylene ketal

To a −78° C. solution of 3.08 ml. (22 mmole) of diisopropylamine in 22 ml. of tetrahydrofuran is added 8.4 ml. (21 mmole) of 2.5M n-butyllithium in hexane. The resultant solution is stirred 30 minutes at −78° C. A solution of 2.10 g. (10 mmole) of decahydro-2,6-naphthalenedione monoethylene ketal in 5 ml. of tetrahydrofuran is slowly added and the resultant solution stirred 30 minutes at −78° C. and 30 minutes at room temperature. The reaction solution is cooled to 0° C. and a solution of 4.79 g. (22 mmole) of diphenyldisulfide is rapidly added. The reaction solution is warmed to room temperarture, stirred one hour and then quenched by addition to 250 ml. ether—250 ml. saturated sodium chloride. The organic extract is dried over magnesium sulfate and evaporated to an oil. The crude oil is purified via column chromatography on 100 g. of silica gel eluted with 50% ether-hexane to yield 947 mg. (crystallized from diisopropyl ether) (30%) of the 3-alpha isomer of the title compound.

MP: 127°-130° C. (from diisopropyl ether).

PMR (CDCl$_3$): delta 0.95-2.4 (m), 2.95 (m, axial methine 1,3 to axial sulfur), 3.70 (m, methine alpha to sulfur), 4.00 (s, ethylene ketal) and 7.30 (m, PhH).

MS (m/e): 318 (M+), 209, 181, 125, 109, 99 and 86.

IR (CHCl$_3$): 1706, 1600 and 1582 cm$^{-1}$.

(b)

3-alpha-Phenylsulfenyl-decahydro-2,6-naphthalenedione 6-monoethylene ketal

To a 0° C. solution of 912 mg. (2.87 mmole) of 3-alpha-phenylthiodecahydro-2,6-naphthalenedione 6-monoethylene ketal in 50 ml. of dichloromethane is slowly added a solution of 494 mg. (2.87 mmole) of m-chloroperoxybenzoic acid in 20 ml. of dichloromethane. The resultant mixture is stirred for two hours at 0° C. to 20° C. and then added to 250 ml. ether—250 ml. 10% sodium sulfite. The organic extract is washed twice with 250 ml. portions of saturated sodium bicarbonate, dried over magnesium sulfate and evaporated to an oil. The crude oil is purified via column chromatography on 50 g. of silica gel eluted with ether to yield 850 mg. (87%) of the title compound as an oily mixture of diastereomers.

PMR (CDCl$_3$): 0.9-2.8 (m), 3.46 (m, methine alpha to sulfur), 3.92 and 4.00 (s, ethylene ketal) and 7.55 (m, PhH).

To a 0° C. slurry of 21.9 g. (0.547 mole) of potassium hydride in 200 ml. of dimethoxyethane was added 43.2 g. (0.277 mole) of methyl phenylsulfinate. To the resultant mixture was added, dropwise over a 30 minute period, a solution of 49.6 g. (0.236 mole) of decahydro-2,6-naphthalenedione monoethylene ketal in 150 ml. of dimethoxyethane. The reaction was stirred one hour at 0° C. and then quenched by the slow addition of 9 ml. (0.5 mole) of water. The quenched reaction mixture was added to 150 ml. ether—150 ml. dichloromethane—125 ml. 6N HCl—375 ml. saturated sodium chloride. The aqueous phase was extracted with another 150 ml. portion of dichloromethane. The combined organic extract was dried over magnesium sulfate and evaporated to a semisolid. It can, if desired, be purified by column chromatography as described above. It can, however, be used as is in the next step (c).

(c) Trans-4a,5,8,8a-tetrahydronaphthalene-2(1H), 6(7H)-dione 6-ethylene ketal.

The crude product obtained by the alternative method under (b) was mixed with 26.8 g. (0.268 mole) of calcium carbonate in one liter of toluene and heated at 110° C. for 30 minutes. The reaction mixture was cooled, filtered through magnesium sulfate and the filtrate evaporated on a rotovapor to yield an oil which was purified via column chromatography on 500 g. of silica gel eluted with 39% ether-hexane to yield 40 g. (81%) of the title compound.

MP: 58°–59° C. (from diisopropyl ether).

IR (CHCl$_3$): 1681, 1658 (shoulder) and 1613 cm$^{-1}$.

PMR (100 MHz, CDCl$_3$): delta 1.32–2.62 (m), 4.00 (s, ethylene ketal), 5.97 (dd, J=10 and 3 Hz, olefin) and 6.71 (dd, J=10 and 2 Hz, olefin).

HRMS (m/e): 208.1099 (M+), 180, 179, 172, 170, 153 and 99 (100%).

Analysis: Calc'd. for C$_{12}$H$_{16}$O$_3$: C, 69.21; H, 7.74. Found: C, 69.11; H, 7.49.

We claim:

1. A compound having the formula

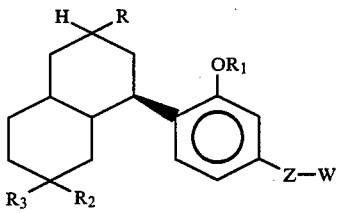

wherein
R is hydroxy or alkanoyloxy having from one to five carbon atoms;
R$_1$ is hydrogen, benzyl or R$_1'$ wherein R$_1'$ is alkanoyl having from one to five carbon atoms, P(O) (OH)$_2$ and mono- and disodium and potassium salts thereof, —CO(CH$_2$)$_2$COOH and the sodium and potassium salts thereof;
R$_2$ when taken individually is hydrogen;
R$_3$ when taken individually is hydrogen, methyl, hydroxy or —OR$_1$;
W is hydrogen, pyridyl, or

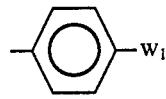

wherein W$_1$ is hydrogen, chloro or fluoro;
when W is hydrogen, Z is
(a) alkylene having from five to thirteen carbon atoms; or
(b) —(alk$_1$)$_m$—O—(alk$_2$)$_n$— wherein each of (alk$_1$) and (alk$_2$) is alkylene having from one to thirteen carbon atoms; each of m and n is 0 or 1; with the provisos that the summation of carbon atoms in (alk$_1$) plus (alk$_2$) is not less than five or greater than thirteen; and at least one of m and n is 1;
when W is other than hydrogen, Z is
(a) alkylene having from three to eight carbon atoms; or
(b) —(alk$_1$)$_m$—O—(alk$_2$)$_n$— wherein each of (alk$_1$) and (alk$_2$) is alkylene having from one to eight carbon atoms; each of m an n is 0 or 1; with the provisos that the summation of carbon atoms in (alk$_1$) plus (alk$_2$) is not less than three or greater than eight; and at least one of m and n is 1; or a pharmaceutically acceptable acid addition salt of those compounds wherein W is pyridyl.

2. A compound of claim 1 wherein R is hydroxy; and R$_1$ is hydrogen or benzyl.

3. A compound according to claim 2 wherein each of R$_2$ and R$_3$ is hydrogen.

4. A compound of claim 2 wherein R$_2$ is hydrogen and R$_3$ is hydroxy.

5. A compound of claim 4 wherein each of R$_1$ and W is hydrogen; and Z is alkylene.

6. The compound of claim 5 wherein Z is —C(CH$_3$)$_2$—(CH$_2$)$_6$.

7. A compound according to claim 3 wherein Z is alkylene and W is hydrogen.

8. A compound according to claim 7 wherein Z is —C(CH$_3$)$_2$—(CH$_2$)$_6$—.

9. The compound according to claim 8 wherein R$_1$ is hydrogen.

10. A compound according to claim 3 wherein Z is —(alk$_1$)$_m$—O—(alk$_2$)$_n$— and W is

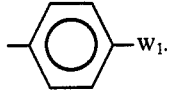

11. A compound according to claim 10 wherein Z is —O—(alk$_2$)— and W$_1$ is hydrogen.

12. The compound according to claim 11 wherein R$_1$ is hydrogen, and Z is —O—CH(CH$_3$)(CH$_2$)$_3$—.

* * * * *

UNITED STATES PATENT AND TRADEMARK OFFICE
CERTIFICATE OF CORRECTION

PATENT NO. : 4,593,131

DATED : June 3, 1986

INVENTOR(S) : Michael R. Johnson and Lawrence S. Melvin, Jr.

It is certified that error appears in the above-identified patent and that said Letters Patent is hereby corrected as shown below:

Column 4, lines 58-66, the formula should appear as follows:

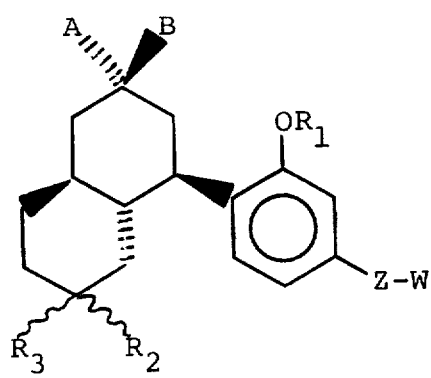

Column 5, lines 20-25, the right hand formula I-A should appear as follows:

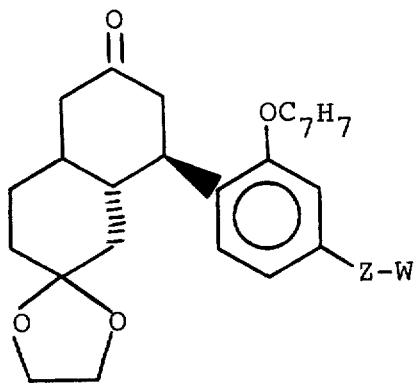

UNITED STATES PATENT AND TRADEMARK OFFICE
CERTIFICATE OF CORRECTION

PATENT NO. : 4,593,131

DATED : June 3, 1986

INVENTOR(S) : Michael R. Johnson and Lawrence S. Melvin, Jr.

It is certified that error appears in the above-identified patent and that said Letters Patent is hereby corrected as shown below:

Column 5, lines 35-40, the left hand formula I-C should appear as follows:

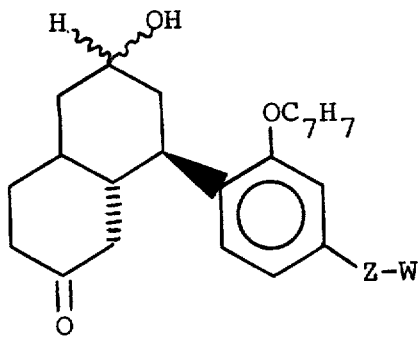

Column 16, lines 60-66, the formula should appear as follows:

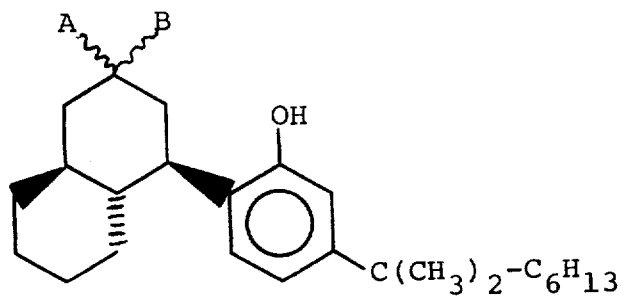

Column 17, Table I, entries 5 and 6 under heading "$R_2$" which read

| H | should read | ◀H |
| ◀H | should read | —H |

UNITED STATES PATENT AND TRADEMARK OFFICE
CERTIFICATE OF CORRECTION

PATENT NO. : 4,593,131

DATED : June 3, 1986

INVENTOR(S) : Michael R. Johnson and Lawrence S. Melvin, Jr.

It is certified that error appears in the above-identified patent and that said Letters Patent is hereby corrected as shown below:

Column 29, lines 43-51, the formula should appear as follows:

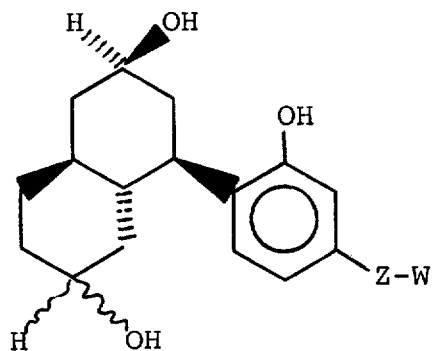

Signed and Sealed this

Eleventh Day of November, 1986

Attest:

DONALD J. QUIGG

Attesting Officer      Commissioner of Patents and Trademarks